(12) United States Patent
Eyal et al.

(10) Patent No.: US 9,976,194 B2
(45) Date of Patent: *May 22, 2018

(54) SUGAR COMPOSITIONS

(71) Applicant: Virdia, Inc., Danville, VA (US)

(72) Inventors: Aharon Eyal, Jerusalem (IL); Robert Jansen, Collinsville, IL (US)

(73) Assignee: Virdia, Inc., Raceland, LA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/730,125

(22) Filed: Jun. 3, 2015

(65) Prior Publication Data

US 2016/0108482 A1 Apr. 21, 2016

Related U.S. Application Data

(63) Continuation of application No. 14/512,321, filed on Oct. 10, 2014, which is a continuation of application
(Continued)

(51) Int. Cl.
*C13K 1/02* (2006.01)
*C13B 50/00* (2011.01)
(Continued)

(52) U.S. Cl.
CPC ............... *C13K 1/02* (2013.01); *A23L 29/30* (2016.08); *C07H 3/02* (2013.01); *C07H 3/04* (2013.01);
(Continued)

(58) Field of Classification Search
CPC .......... C13K 1/02; C13K 11/00; C13K 13/00; C13K 13/002
See application file for complete search history.

(56) References Cited

U.S. PATENT DOCUMENTS

| 1,344,671 A | 6/1920 | Bergius |
| 1,544,149 A | 6/1925 | Hagglund |

(Continued)

FOREIGN PATENT DOCUMENTS

| CA | 2735396 A1 | 3/2010 |
| CN | 1353310 A | 6/2002 |

(Continued)

OTHER PUBLICATIONS

Office action dated Jan. 29, 2016 for U.S. Appl. No. 14/385,142.
(Continued)

*Primary Examiner* — Melvin C. Mayes
*Assistant Examiner* — Stefanie J Cohen
(74) *Attorney, Agent, or Firm* — Wilson Sonsini Goodrich & Rosati

(57) ABSTRACT

A sugar composition comprising at least 40% dissolved solids in an aqueous solution having a viscosity at least 10% lower than a 42 DE (Dextrose Equivalents) reference solution with a same dissolved solids concentration at a given temperature. Another sugar composition comprising at least 30% glucose relative to total sugars, at least 10% mannose relative to total sugars, at least 5% xylose relative to total sugars, and less than 0.25% ash. Another sugar composition comprising at least 30% glucose relative to total sugars at least 10% mannose relative to total sugars, at least 5% xylose relative to total sugars, and at least 2% total furfurals.

39 Claims, 2 Drawing Sheets

Related U.S. Application Data

No. 14/385,142, filed as application No. PCT/US2012/059542 on Oct. 10, 2012, now Pat. No. 9,617,608.

(60) Provisional application No. 61/545,389, filed on Oct. 10, 2011.

(51) Int. Cl.
| C13K 13/00 | (2006.01) |
|---|---|
| C07H 3/02 | (2006.01) |
| C07H 3/06 | (2006.01) |
| C07H 3/04 | (2006.01) |
| C13K 11/00 | (2006.01) |
| A23L 29/30 | (2016.01) |

(52) U.S. Cl.
CPC .............. *C07H 3/06* (2013.01); *C13B 50/00* (2013.01); *C13K 11/00* (2013.01); *C13K 13/00* (2013.01); *C13K 13/002* (2013.01)

(56) References Cited

U.S. PATENT DOCUMENTS

| | | |
|---|---|---|
| 2,008,284 A | 7/1935 | Friedrich et al. |
| 2,239,095 A | 4/1941 | Hasche |
| 2,440,442 A | 4/1948 | Hillyer et al. |
| 2,752,270 A | 6/1956 | Specht |
| 2,890,972 A | 6/1959 | Wheaton |
| 2,917,390 A | 12/1959 | Apel et al. |
| 2,944,923 A | 7/1960 | Riehm |
| 2,989,569 A | 6/1961 | Apel |
| 3,132,051 A | 5/1964 | Nobile et al. |
| 3,616,222 A | 10/1971 | Dasinger |
| 3,839,318 A | 10/1974 | Mansfield |
| 3,990,904 A | 11/1976 | Friese et al. |
| 4,029,515 A | 6/1977 | Kiminki et al. |
| 4,102,705 A | 7/1978 | Pfeiffer et al. |
| 4,105,467 A | 8/1978 | Buckl et al. |
| 4,165,240 A | 8/1979 | Enokizono et al. |
| 4,174,976 A | 11/1979 | Tsao et al. |
| 4,237,110 A | 12/1980 | Forster et al. |
| 4,266,981 A | 5/1981 | Tsao et al. |
| 4,277,626 A | 7/1981 | Forss et al. |
| 4,278,471 A | 7/1981 | Whittingham |
| 4,291,007 A | 9/1981 | Baniel |
| 4,299,677 A | 11/1981 | Venkatasubramanian et al. |
| 4,395,543 A | 7/1983 | Wang et al. |
| 4,425,136 A | 1/1984 | Pearson et al. |
| 4,445,938 A | 5/1984 | Verwaerde et al. |
| 4,470,851 A | 9/1984 | Paszner et al. |
| 4,472,501 A | 9/1984 | Takasawa et al. |
| 4,496,426 A | 1/1985 | Baumeister et al. |
| 4,503,278 A | 3/1985 | Chen et al. |
| 4,520,105 A | 5/1985 | Sinner et al. |
| 4,525,218 A | 6/1985 | Chen et al. |
| 4,556,430 A | 12/1985 | Converse et al. |
| 4,579,595 A | 4/1986 | Sachetto et al. |
| 4,608,245 A | 8/1986 | Gaddy et al. |
| 4,612,286 A | 9/1986 | Sherman et al. |
| 4,615,742 A | 10/1986 | Wright |
| 4,677,198 A | 6/1987 | Linnett et al. |
| 4,701,414 A | 10/1987 | Van et al. |
| 4,713,413 A | 12/1987 | Tegge et al. |
| 4,746,401 A | 5/1988 | Roberts et al. |
| 4,764,596 A | 8/1988 | Lora et al. |
| 4,840,903 A | 6/1989 | Wu |
| 4,901,635 A | 2/1990 | Williams |
| 4,934,177 A | 6/1990 | Cuthbertson et al. |
| 4,992,308 A | 2/1991 | Sunol |
| 5,049,494 A | 9/1991 | Allenza |
| 5,081,026 A | 1/1992 | Heikkilae et al. |
| 5,114,491 A | 5/1992 | Sarhaddar |
| 5,205,473 A | 4/1993 | Coffin, Sr. |
| 5,227,446 A | 7/1993 | Denzinger et al. |
| 5,244,553 A | 9/1993 | Goldstein |
| 5,332,842 A | 7/1994 | Dickakian |
| 5,370,997 A | 12/1994 | Antranikian et al. |
| 5,407,580 A | 4/1995 | Hester et al. |
| 5,411,594 A | 5/1995 | Brelsford |
| 5,421,964 A | 6/1995 | Mahler et al. |
| 5,424,417 A | 6/1995 | Torget et al. |
| 5,538,637 A | 7/1996 | Hester et al. |
| 5,580,389 A | 12/1996 | Farone et al. |
| 5,597,714 A | 1/1997 | Farone et al. |
| 5,696,195 A | 12/1997 | Stabel et al. |
| 5,705,369 A | 1/1998 | Torget et al. |
| 5,711,817 A | 1/1998 | Titmas |
| 5,726,046 A | 3/1998 | Farone et al. |
| 5,730,837 A | 3/1998 | Black et al. |
| 5,730,877 A | 3/1998 | Heikkila et al. |
| 5,782,982 A | 7/1998 | Farone et al. |
| 5,820,687 A | 10/1998 | Farone et al. |
| 5,837,831 A | 11/1998 | Gruning |
| 5,846,787 A | 12/1998 | Ladisch et al. |
| 5,856,261 A | 1/1999 | Culross et al. |
| 5,865,948 A | 2/1999 | Lora et al. |
| 5,876,505 A | 3/1999 | Klyosov et al. |
| 5,969,195 A | 10/1999 | Stabel et al. |
| 5,980,640 A | 11/1999 | Nurmi et al. |
| 6,001,410 A | 12/1999 | Bolen et al. |
| 6,007,636 A | 12/1999 | Lightner |
| 6,022,419 A | 2/2000 | Torget et al. |
| 6,063,204 A | 5/2000 | Hester et al. |
| 6,086,681 A | 7/2000 | Lindroos et al. |
| 6,124,443 A | 9/2000 | Darsow |
| 6,136,868 A | 10/2000 | Culross et al. |
| 6,224,776 B1 | 5/2001 | Heikkila et al. |
| 6,239,274 B1 | 5/2001 | Heikkila et al. |
| 6,258,175 B1 | 7/2001 | Lightner |
| 6,391,204 B1 | 5/2002 | Russo, Jr. |
| 6,419,788 B1 | 7/2002 | Wingerson |
| 6,419,828 B1 | 7/2002 | Russo, Jr. |
| 6,479,713 B1 | 11/2002 | Werpy et al. |
| 6,486,366 B1 | 11/2002 | Ostgard et al. |
| 6,548,662 B1 | 4/2003 | Ohsaki et al. |
| 6,572,775 B2 | 6/2003 | Heikkila et al. |
| 6,620,292 B2 | 9/2003 | Wingerson |
| 6,692,578 B2 | 2/2004 | Schmidt et al. |
| 6,747,076 B2 | 6/2004 | Schneider et al. |
| 6,752,902 B2 | 6/2004 | Heikkila et al. |
| 6,824,599 B2 | 11/2004 | Swatloski et al. |
| 6,841,085 B2 | 1/2005 | Werpy et al. |
| 6,852,345 B2 | 2/2005 | Hill et al. |
| 6,872,316 B2 | 3/2005 | Heikkila et al. |
| 6,875,349 B2 | 4/2005 | Heikkila et al. |
| 6,896,811 B2 | 5/2005 | Heikkila et al. |
| 6,924,371 B2 | 8/2005 | Karki et al. |
| 6,936,110 B2 | 8/2005 | Van Thorre |
| 6,942,754 B2 | 9/2005 | Izumi et al. |
| 7,022,239 B2 | 4/2006 | Heikkila et al. |
| 7,026,152 B2 | 4/2006 | Ingram et al. |
| 7,038,094 B2 | 5/2006 | Werpy et al. |
| 7,109,005 B2 | 9/2006 | Eroma et al. |
| 7,198,925 B2 | 4/2007 | Foody |
| 7,229,558 B2 | 6/2007 | Heikkila et al. |
| 7,361,273 B2 | 4/2008 | Heikkila et al. |
| 7,399,323 B2 | 7/2008 | Renninger et al. |
| 7,465,791 B1 | 12/2008 | Hallberg et al. |
| 7,501,025 B2 | 3/2009 | Bakker et al. |
| 7,503,981 B2 | 3/2009 | Wyman et al. |
| 7,524,660 B2 | 4/2009 | Caimi et al. |
| 7,649,086 B2 | 1/2010 | Belanger et al. |
| 7,699,958 B2 | 4/2010 | Griffith et al. |
| 7,704,381 B2 | 4/2010 | Siekmann et al. |
| 7,713,725 B2 | 5/2010 | England et al. |
| 7,717,364 B2 | 5/2010 | Wingerson |
| 7,718,070 B2 | 5/2010 | Mahnon |
| 7,880,049 B2 | 2/2011 | Dumesic et al. |
| 7,901,511 B2 | 3/2011 | Griffin et al. |
| 7,935,156 B2 | 5/2011 | Renninger et al. |
| 7,942,940 B2 | 5/2011 | Renninger et al. |
| 7,947,858 B2 | 5/2011 | Buchert |
| 7,959,811 B2 | 6/2011 | Airaksinen et al. |

(56) References Cited

U.S. PATENT DOCUMENTS

| | | |
|---|---|---|
| 7,977,517 B2 | 7/2011 | Cortright et al. |
| 7,993,709 B2 | 8/2011 | Brunet |
| 8,017,818 B2 | 9/2011 | Cortright et al. |
| 8,022,260 B2 | 9/2011 | O'Connor et al. |
| 8,026,378 B2 | 9/2011 | Selifonov |
| 8,030,039 B1 | 10/2011 | Retsina et al. |
| 8,052,953 B2 | 11/2011 | Chen |
| 8,053,468 B2 | 11/2011 | Selifonov |
| 8,084,508 B2 | 12/2011 | Yakobson et al. |
| 8,084,635 B2 | 12/2011 | Selifonov |
| 8,101,808 B2 | 1/2012 | Evanko et al. |
| 8,152,867 B2 | 4/2012 | Dumenil |
| 8,163,092 B2 | 4/2012 | Baniel et al. |
| 8,178,701 B2 | 5/2012 | Selifonov |
| 8,188,030 B2 | 5/2012 | Rieth et al. |
| 8,277,643 B2 | 10/2012 | Huber et al. |
| 8,404,355 B2 | 3/2013 | Jansen et al. |
| 8,500,910 B2 | 8/2013 | Brady et al. |
| 8,637,660 B2 | 1/2014 | Fanselow et al. |
| 8,637,661 B2 | 1/2014 | Fanselow et al. |
| 8,657,960 B2 | 2/2014 | North |
| 8,685,685 B2 | 4/2014 | Retsina et al. |
| 8,722,878 B2 | 5/2014 | Raines et al. |
| 8,894,771 B2 | 11/2014 | Floyd et al. |
| 8,999,065 B2 | 4/2015 | Kazachkin et al. |
| 9,200,337 B2 | 12/2015 | Colakyan et al. |
| 9,243,303 B2 | 1/2016 | Fang |
| 9,410,216 B2 | 8/2016 | Eyal et al. |
| 9,476,106 B2 | 10/2016 | Eyal et al. |
| 9,512,495 B2 | 12/2016 | Eyal et al. |
| 2002/0069981 A1 | 6/2002 | Speaks et al. |
| 2002/0096274 A1 | 7/2002 | Lindstrom et al. |
| 2002/0153317 A1 | 10/2002 | Heikkila et al. |
| 2002/0159990 A1 | 10/2002 | Ingram et al. |
| 2003/0094416 A1 | 5/2003 | Heikkila et al. |
| 2003/0192660 A1 | 10/2003 | Speaks et al. |
| 2003/0199049 A1 | 10/2003 | Nguyen et al. |
| 2003/0222021 A1 | 12/2003 | Ennelin et al. |
| 2004/0108085 A1 | 6/2004 | Kettenbach et al. |
| 2004/0121446 A1 | 6/2004 | England et al. |
| 2004/0127371 A1 | 7/2004 | Arrowsmith et al. |
| 2004/0199049 A1 | 10/2004 | Parasher et al. |
| 2004/0231661 A1 | 11/2004 | Griffin et al. |
| 2004/0237499 A1 | 12/2004 | Yogev et al. |
| 2005/0034823 A1 | 2/2005 | Brelid et al. |
| 2005/0069998 A1 | 3/2005 | Ballesteros Perdices et al. |
| 2005/0148056 A1 | 7/2005 | Levine et al. |
| 2005/0244934 A1 | 11/2005 | Foody et al. |
| 2006/0024801 A1 | 2/2006 | Holtzapple et al. |
| 2006/0051812 A1 | 3/2006 | Helin et al. |
| 2006/0207734 A1 | 9/2006 | Day et al. |
| 2006/0281913 A1 | 12/2006 | Ferreira et al. |
| 2007/0020375 A1 | 1/2007 | Jansen et al. |
| 2007/0031953 A1 | 2/2007 | Dunson, Jr. et al. |
| 2007/0053987 A1 | 3/2007 | Bayer et al. |
| 2007/0112187 A1 | 5/2007 | Heikkila et al. |
| 2007/0184555 A1 | 8/2007 | Banavali et al. |
| 2007/0219521 A1 | 9/2007 | Hird et al. |
| 2007/0254348 A1 | 11/2007 | Retsina et al. |
| 2008/0029233 A1 | 2/2008 | Wingerson et al. |
| 2008/0032344 A1 | 2/2008 | Fallavollita |
| 2008/0041366 A1 | 2/2008 | Wahnon |
| 2008/0057555 A1 | 3/2008 | Nguyen |
| 2008/0102502 A1 | 5/2008 | Foody et al. |
| 2008/0168982 A1 | 7/2008 | Vente et al. |
| 2008/0182305 A1 | 7/2008 | Foody et al. |
| 2008/0202504 A1 | 8/2008 | Hilst |
| 2008/0210393 A1 | 9/2008 | Gutierrez-Suarez et al. |
| 2008/0216391 A1 | 9/2008 | Cortright et al. |
| 2008/0227161 A1 | 9/2008 | Levie et al. |
| 2008/0274528 A1 | 11/2008 | Dixon et al. |
| 2008/0292766 A1 | 11/2008 | Hoffman et al. |
| 2008/0300434 A1 | 12/2008 | Cortright et al. |
| 2008/0300435 A1 | 12/2008 | Cortright et al. |
| 2008/0305210 A1 | 12/2008 | Petersen |
| 2009/0053783 A1 | 2/2009 | Gokarn et al. |
| 2009/0056889 A1 | 3/2009 | Ren et al. |
| 2009/0062232 A1 | 3/2009 | Fujikawa et al. |
| 2009/0124829 A1 | 5/2009 | Gong |
| 2009/0142848 A1 | 6/2009 | Wyman et al. |
| 2009/0155873 A1 | 6/2009 | Kashiyama et al. |
| 2009/0173339 A1 | 7/2009 | Heikkilae et al. |
| 2009/0176286 A1 | 7/2009 | O'Connor et al. |
| 2009/0176979 A1 | 7/2009 | Hara et al. |
| 2009/0215718 A1 | 8/2009 | Van Laere et al. |
| 2009/0218055 A1 | 9/2009 | Unsitalo et al. |
| 2009/0226979 A1 | 9/2009 | Retsina et al. |
| 2009/0226993 A1 | 9/2009 | Kumar et al. |
| 2009/0229599 A1 | 9/2009 | Zhang et al. |
| 2009/0232892 A1 | 9/2009 | Yamasaki et al. |
| 2009/0286295 A1 | 11/2009 | Medoff et al. |
| 2009/0305942 A1 | 12/2009 | Day et al. |
| 2010/0009408 A1 | 1/2010 | England et al. |
| 2010/0024807 A1 | 2/2010 | Burke et al. |
| 2010/0028557 A1 | 2/2010 | Nagano |
| 2010/0043782 A1 | 2/2010 | Kilambi et al. |
| 2010/0043784 A1 | 2/2010 | Jensen |
| 2010/0048884 A1 | 2/2010 | Kilambi |
| 2010/0048924 A1 | 2/2010 | Kilambi |
| 2010/0069626 A1 | 3/2010 | Kilambi |
| 2010/0083565 A1 | 4/2010 | Gruter |
| 2010/0086981 A1 | 4/2010 | Latouf et al. |
| 2010/0093995 A1 | 4/2010 | Baniel et al. |
| 2010/0116267 A1 | 5/2010 | Mraz et al. |
| 2010/0124772 A1 | 5/2010 | Sabesan |
| 2010/0136634 A1 | 6/2010 | Kratochvil et al. |
| 2010/0136642 A1 | 6/2010 | Belanger et al. |
| 2010/0151527 A1 | 6/2010 | Endo et al. |
| 2010/0163019 A1 | 7/2010 | Chornet et al. |
| 2010/0170504 A1 | 7/2010 | Zhang |
| 2010/0184151 A1 | 7/2010 | Tolan et al. |
| 2010/0184176 A1 | 7/2010 | Ishida et al. |
| 2010/0189706 A1 | 7/2010 | Chang et al. |
| 2010/0203605 A1 | 8/2010 | Kim et al. |
| 2010/0233761 A1 | 9/2010 | Czartoski et al. |
| 2010/0268000 A1 | 10/2010 | Parekh et al. |
| 2010/0269990 A1 | 10/2010 | Dottori et al. |
| 2010/0279354 A1* | 11/2010 | de Crecy .............. C12P 7/6463 435/71.1 |
| 2010/0279361 A1 | 11/2010 | South et al. |
| 2010/0279372 A1 | 11/2010 | Cho et al. |
| 2010/0297704 A1 | 11/2010 | Li |
| 2010/0305241 A1 | 12/2010 | Balakshin et al. |
| 2010/0305242 A1 | 12/2010 | Balakshin et al. |
| 2010/0305243 A1 | 12/2010 | Balakshin et al. |
| 2010/0305244 A1 | 12/2010 | Balakshin et al. |
| 2010/0313882 A1 | 12/2010 | Dottori et al. |
| 2011/0003348 A1 | 1/2011 | Genta et al. |
| 2011/0003352 A1 | 1/2011 | Retsina et al. |
| 2011/0020910 A1 | 1/2011 | Glass et al. |
| 2011/0028710 A1 | 2/2011 | Baniel et al. |
| 2011/0033896 A1* | 2/2011 | Boy ..................... C12P 19/02 435/71.1 |
| 2011/0059316 A1 | 3/2011 | Kilambi et al. |
| 2011/0060132 A1 | 3/2011 | Lewis |
| 2011/0061645 A1 | 3/2011 | Fosdick et al. |
| 2011/0065159 A1 | 3/2011 | Raines et al. |
| 2011/0070131 A1 | 3/2011 | Schmidt et al. |
| 2011/0097776 A1 | 4/2011 | Johnson |
| 2011/0100359 A1 | 5/2011 | North |
| 2011/0105737 A1 | 5/2011 | Benjelloun Mlayah et al. |
| 2011/0124057 A1 | 5/2011 | Genta et al. |
| 2011/0129880 A1 | 6/2011 | Conners et al. |
| 2011/0129886 A1 | 6/2011 | Howard et al. |
| 2011/0143411 A1 | 6/2011 | Yuan et al. |
| 2011/0143412 A1 | 6/2011 | Kim et al. |
| 2011/0146138 A1 | 6/2011 | Berry et al. |
| 2011/0155559 A1 | 6/2011 | Medoff |
| 2011/0178290 A1 | 7/2011 | Baniel et al. |
| 2011/0183394 A1 | 7/2011 | Bell et al. |
| 2011/0201059 A1 | 8/2011 | Hall et al. |
| 2011/0256615 A1 | 10/2011 | Brady et al. |
| 2011/0262984 A1* | 10/2011 | Nguyen ................. F23C 13/02 435/165 |

(56) References Cited

U.S. PATENT DOCUMENTS

| | | |
|---|---|---|
| 2011/0268652 A1 | 11/2011 | Machhammer et al. |
| 2011/0271875 A1 | 11/2011 | Ahmed et al. |
| 2011/0275860 A1 | 11/2011 | Beldring et al. |
| 2011/0281298 A1 | 11/2011 | Rawls et al. |
| 2011/0300617 A1 | 12/2011 | Genta et al. |
| 2011/0314726 A1 | 12/2011 | Jameel et al. |
| 2011/0318796 A1 | 12/2011 | Walther |
| 2012/0006320 A1 | 1/2012 | Nguyen |
| 2012/0023810 A1 | 2/2012 | Fjare et al. |
| 2012/0036768 A1 | 2/2012 | Phillips et al. |
| 2012/0040408 A1 | 2/2012 | Decker et al. |
| 2012/0055466 A1 | 3/2012 | Cotti et al. |
| 2012/0058526 A1 | 3/2012 | Jansen et al. |
| 2012/0104313 A1 | 5/2012 | Garbero et al. |
| 2012/0116063 A1 | 5/2012 | Jansen et al. |
| 2012/0122170 A1 | 5/2012 | Ropars et al. |
| 2012/0134912 A1 | 5/2012 | Baniel et al. |
| 2012/0135489 A1 | 5/2012 | Weydahl |
| 2012/0156517 A1 | 6/2012 | Vuori et al. |
| 2012/0167874 A1 | 7/2012 | Jansen et al. |
| 2012/0184026 A1 | 7/2012 | Eyal |
| 2012/0227733 A1 | 9/2012 | Eyal et al. |
| 2012/0240921 A1 | 9/2012 | Fukuoka et al. |
| 2012/0264873 A1 | 10/2012 | Eyal et al. |
| 2012/0279497 A1 | 11/2012 | Jansen et al. |
| 2012/0282655 A1 | 11/2012 | Gibbs |
| 2012/0289692 A1 | 11/2012 | Gray et al. |
| 2012/0308991 A1 | 12/2012 | Eiteman et al. |
| 2012/0323053 A1 | 12/2012 | Qiao et al. |
| 2013/0012610 A1 | 1/2013 | Belanger et al. |
| 2013/0028832 A1 | 1/2013 | Eyal et al. |
| 2013/0028833 A1 | 1/2013 | Eyal et al. |
| 2013/0047979 A1 | 2/2013 | Eyal et al. |
| 2013/0115653 A1 | 5/2013 | Peterson et al. |
| 2013/0167836 A1 | 7/2013 | Floyd et al. |
| 2013/0167837 A1 | 7/2013 | Floyd et al. |
| 2013/0216693 A1 | 8/2013 | Harrison et al. |
| 2013/0252312 A1 | 9/2013 | Yoshikuni et al. |
| 2013/0276778 A1 | 10/2013 | Jansen et al. |
| 2013/0295628 A1 | 11/2013 | Retsina et al. |
| 2014/0011248 A1 | 1/2014 | Medoff et al. |
| 2014/0123973 A1 | 5/2014 | North |
| 2014/0154759 A1 | 6/2014 | Retsina et al. |
| 2014/0162345 A1 | 6/2014 | Eyal |
| 2014/0171379 A1 | 6/2014 | Jansen et al. |
| 2014/0175331 A1 | 6/2014 | Jansen et al. |
| 2014/0202452 A1 | 7/2014 | Jansen et al. |
| 2014/0220651 A1 | 8/2014 | Raines et al. |
| 2014/0227161 A1 | 8/2014 | Manesh et al. |
| 2014/0242867 A1 | 8/2014 | Jansen et al. |
| 2014/0309416 A1 | 10/2014 | Teixeira et al. |
| 2014/0316162 A1 | 10/2014 | Gao et al. |
| 2015/0020797 A1 | 1/2015 | Eyal |
| 2015/0028255 A1 | 1/2015 | Eyal et al. |
| 2015/0048274 A1 | 2/2015 | Eyal |
| 2015/0144126 A1 | 5/2015 | Jansen et al. |
| 2015/0176090 A1 | 6/2015 | Dumesic et al. |
| 2015/0184261 A1 | 7/2015 | Floyd et al. |
| 2015/0197824 A1 | 7/2015 | Floyd et al. |
| 2015/0299738 A1 | 10/2015 | Wang et al. |
| 2016/0108481 A1 | 4/2016 | Eyal et al. |
| 2016/0222477 A1 | 8/2016 | Jansen et al. |
| 2016/0376546 A1 | 12/2016 | Eyal et al. |
| 2017/0130282 A1 | 5/2017 | Eyal et al. |

FOREIGN PATENT DOCUMENTS

| | | | |
|---|---|---|---|
| CN | 1505682 A | | 6/2004 |
| CN | 101613970 A | | 12/2009 |
| CN | 101824054 A | | 9/2010 |
| CN | 102239184 A | | 11/2011 |
| CN | 102433358 B | | 10/2013 |
| DE | 1955392 A1 | | 6/1971 |
| EP | 0317036 A1 | | 5/1989 |
| EP | 0814676 A1 | | 1/1998 |
| EP | 0690931 B1 | | 10/2001 |
| EP | 1304412 A2 | | 4/2003 |
| EP | 1458805 B1 | | 8/2011 |
| EP | 1733282 B1 | | 1/2012 |
| EP | 2325246 B1 | | 11/2013 |
| GB | 1562682 A | | 3/1980 |
| GB | 2488918 B | | 3/2014 |
| JP | S5141451 A | | 4/1976 |
| JP | 2835894 B2 | | 12/1998 |
| JP | 2002177000 A | | 6/2002 |
| JP | 2005023041 A | | 1/2005 |
| JP | 2006101829 A | | 4/2006 |
| JP | 2006223152 A | | 8/2006 |
| JP | 2008035853 A | | 2/2008 |
| JP | 2011103874 A | | 6/2011 |
| KR | 20140108301 A | | 9/2014 |
| RU | 2313572 C2 | | 12/2007 |
| WO | WO 82/01723 A1 | | 5/1982 |
| WO | WO 93/05186 A1 | | 3/1993 |
| WO | WO-9426380 A1 | | 11/1994 |
| WO | WO-0061276 A1 | | 10/2000 |
| WO | WO 01/25143 A1 | | 4/2001 |
| WO | WO 01/32715 A1 | | 5/2001 |
| WO | WO 02/02826 A1 | | 1/2002 |
| WO | WO 02/053783 A1 | | 7/2002 |
| WO | WO 02/070753 A2 | | 9/2002 |
| WO | WO-03010339 A1 | | 2/2003 |
| WO | WO03010339 A1 | * | 3/2003 |
| WO | WO 2004/003236 A1 | | 1/2004 |
| WO | WO-2004013409 A1 | | 2/2004 |
| WO | WO 2004/050983 A1 | | 6/2004 |
| WO | WO 2006/006164 A2 | | 1/2006 |
| WO | WO 2006/034581 A1 | | 4/2006 |
| WO | WO 2006/038863 A1 | | 4/2006 |
| WO | WO 2006/056838 A1 | | 6/2006 |
| WO | WO 2006/086861 A2 | | 8/2006 |
| WO | WO 2006/086861 A3 | | 10/2006 |
| WO | WO 2007/019505 A2 | | 2/2007 |
| WO | WO 2007/019505 A3 | | 6/2007 |
| WO | WO07102638 | * | 9/2007 |
| WO | WO-2007102638 A1 | | 9/2007 |
| WO | WO 2007/112314 A2 | | 10/2007 |
| WO | WO 2007/112314 A3 | | 11/2007 |
| WO | WO-2007130984 A2 | | 11/2007 |
| WO | WO 2008/019468 A1 | | 2/2008 |
| WO | WO 2008/027699 A2 | | 3/2008 |
| WO | WO 2008/069830 A2 | | 6/2008 |
| WO | WO 2008/027699 A3 | | 7/2008 |
| WO | WO 2008/109877 A1 | | 9/2008 |
| WO | WO 2008/111045 A1 | | 9/2008 |
| WO | WO 2008/123419 A1 | | 10/2008 |
| WO | WO 2008/131229 A1 | | 10/2008 |
| WO | WO 2008/069830 A3 | | 11/2008 |
| WO | WO 2008/137639 A1 | | 11/2008 |
| WO | WO 2008/144903 A1 | | 12/2008 |
| WO | WO 2009/003292 A1 | | 1/2009 |
| WO | WO 2009/015663 A2 | | 2/2009 |
| WO | WO 2009/020459 A2 | | 2/2009 |
| WO | WO 2009/030713 A1 | | 3/2009 |
| WO | WO 2009/031164 A1 | | 3/2009 |
| WO | WO 2009/036674 A1 | | 3/2009 |
| WO | WO 2009/020459 A3 | | 4/2009 |
| WO | WO 2006/006164 A3 | | 5/2009 |
| WO | WO-2009060126 A1 | | 5/2009 |
| WO | WO 2009/125400 A2 | | 10/2009 |
| WO | WO 2009/135480 A1 | | 11/2009 |
| WO | WO 2009/142837 A2 | | 11/2009 |
| WO | WO-2009137839 A1 | | 11/2009 |
| WO | WO 2009/015663 A3 | | 12/2009 |
| WO | WO-2009154447 A1 | | 12/2009 |
| WO | WO2009155982 | * | 12/2009 |
| WO | WO-2009155982 A1 | | 12/2009 |
| WO | WO 2009/125400 A3 | | 1/2010 |
| WO | WO 2010/006840 A2 | | 1/2010 |
| WO | WO 2010/009343 A2 | | 1/2010 |
| WO | WO 2010/015404 A1 | | 2/2010 |
| WO | WO 2010/020977 A2 | | 2/2010 |
| WO | WO 2009/142837 A3 | | 3/2010 |
| WO | WO 2010/026244 A1 | | 3/2010 |

(56) References Cited

FOREIGN PATENT DOCUMENTS

| | | |
|---|---|---|
| WO | WO 2010/026572 A1 | 3/2010 |
| WO | WO 2010/009343 A3 | 4/2010 |
| WO | WO 2010/034055 A1 | 4/2010 |
| WO | WO 2010/038021 A2 | 4/2010 |
| WO | WO 2010/043424 A1 | 4/2010 |
| WO | WO 2010/046619 A1 | 4/2010 |
| WO | WO-2010045576 A2 | 4/2010 |
| WO | WO-2010046532 A1 | 4/2010 |
| WO | WO 2010/006840 A3 | 5/2010 |
| WO | WO 2010/064229 A2 | 6/2010 |
| WO | WO 2010/064229 A3 | 7/2010 |
| WO | WO 2010/081231 A1 | 7/2010 |
| WO | WO 2010/038021 A3 | 8/2010 |
| WO | WO 2010/020977 A3 | 10/2010 |
| WO | WO 2010/113129 A2 | 10/2010 |
| WO | WO 2010/113129 A3 | 10/2010 |
| WO | WO 2010/113130 A2 | 10/2010 |
| WO | WO 2010/122554 A1 | 10/2010 |
| WO | WO 2010/128272 A1 | 11/2010 |
| WO | WO 2010/135804 A1 | 12/2010 |
| WO | WO 2010/135805 A1 | 12/2010 |
| WO | WO 2010/135806 A1 | 12/2010 |
| WO | WO 2010/135807 A1 | 12/2010 |
| WO | WO 2010/135832 A1 | 12/2010 |
| WO | WO 2010/135833 A1 | 12/2010 |
| WO | WO 2010/146331 A2 | 12/2010 |
| WO | WO 2010/113130 A3 | 1/2011 |
| WO | WO 2011/002660 A1 | 1/2011 |
| WO | WO 2011/007043 A1 | 1/2011 |
| WO | WO 2011/007369 A1 | 1/2011 |
| WO | WO 2011/017587 A1 | 2/2011 |
| WO | WO 2011/028554 A1 | 3/2011 |
| WO | WO 2011/039751 A2 | 4/2011 |
| WO | WO 2011/066487 A1 | 6/2011 |
| WO | WO 2011/070602 A1 | 6/2011 |
| WO | WO 2011/080131 A2 | 7/2011 |
| WO | WO 2011/089589 A1 | 7/2011 |
| WO | WO-2011091044 A1 | 7/2011 |
| WO | WO 2011/097719 A1 | 8/2011 |
| WO | WO 2011/080131 A3 | 9/2011 |
| WO | WO 2011/111189 A1 | 9/2011 |
| WO | WO 2011/111190 A1 | 9/2011 |
| WO | WO 2010/146331 A3 | 10/2011 |
| WO | WO 2011/039751 A3 | 10/2011 |
| WO | WO 2011/140222 A1 | 11/2011 |
| WO | WO 2011/151823 A1 | 12/2011 |
| WO | WO 2011/163084 A1 | 12/2011 |
| WO | WO-2011154604 A1 | 12/2011 |
| WO | WO 2012/001688 A2 | 1/2012 |
| WO | WO 2012/015575 A1 | 2/2012 |
| WO | WO 2012/061085 A2 | 5/2012 |
| WO | WO 2012/106727 A1 | 8/2012 |
| WO | WO 2013/038399 A1 | 3/2013 |
| WO | WO 2013/040702 A1 | 3/2013 |
| WO | WO-2013055785 A1 | 4/2013 |
| WO | WO-2013070969 A2 | 5/2013 |
| WO | WO 2013/083876 A2 | 6/2013 |
| WO | WO-2013166469 A2 | 11/2013 |
| WO | WO 2013/192572 A1 | 12/2013 |
| WO | WO 2014/044753 A1 | 3/2014 |
| WO | WO-2014081605 A1 | 5/2014 |
| WO | WO 2012/081740 A1 | 6/2014 |
| WO | WO 2014/138553 A1 | 9/2014 |
| WO | WO 2014/169079 A2 | 10/2014 |
| WO | WO 2012/079021 A2 | 6/2015 |
| WO | WO-2015139141 A1 | 9/2015 |

OTHER PUBLICATIONS

Office action dated Jun. 25, 2015 for U.S. Appl. No. 14/385,142.
U.S. Appl. No. 61/473,134, filed Apr. 7, 2011, Eyal.
U.S. Appl. No. 61/524,350, filed Aug. 17, 2011, Eyal et al.
U.S. Appl. No. 61/528,257, filed Aug. 28, 2011, Jansen et al.
U.S. Appl. No. 61/539,196, filed Sep. 26, 2011, Jansen et al.
U.S. Appl. No. 61/539,239, filed Sep. 26, 2011, Jansen et al.
U.S. Appl. No. 61/539,272, filed Sep. 26, 2011, Jansen et al.
U.S. Appl. No. 14/730,118, filed Jun. 3, 2015, Eyal et al.
Aden, et al. Lignocellulosic Biomass to Ethanol Process Design and Economics Utilizing Co-Current Dilute Acid Prehydrolysis and Enzymatic Hydrolysis for Corn Stover. National Renewable Energy Laboratory, NREL is a U.S. Department of Energy LaboratoryOperated by Midwest Research Institute. Jun. 2002.
ADM corn 42/43 syrup. Typical data information. Accessed Oct. 5, 2012.
Ahmed, et al. Preparation and studies on immobilized α-glucosidase from baker's yeast Saccharomyces cerevisiae. J. Serb. Chem. Soc. 2007; 72(12):1255-1263.
Amidon, et al. Biorefinery: Conversion of Woody Biomass to Chemicals, Energy and Materials. Journal of Biobased Materials and Bioenergy. 2008; 2:100-120.
Antonoplis, et al. High pressure HCl conversion of cellulose to glucose. Lawrence Berkeley National Laboratory, University of California, Paper LBL,14221. Aug. 1981.
ASTM Standards. Standard Test Method for Ash in Biomass. Designation: E1755-01 (Reapproved 2007).
Atalla, et al. Analysis of Lignin and Cellulose in Biological Energy Sources by Raman Microscopy. 2011.
Badger. Ethanol from cellulose: a general review. Trends in new crops and new uses. 2002; 17-21.
Barton. CRC handbook of solubility parameters and other cohesion parameters. CRC Press. Boca Raton. 1991; 122-138.
Beck, et al. Production of ethanol by bioconversion of wood sugars derived from two-stage dilute acid hydrolysis of hardwood. Biomass. 1984; 6:101-110.
Bergius. Conversion of wood to carbohydrates and problems in the industrial use of concentrated hydrochloric acid. Industrial and Engineering chemistry. 1937; 29(3):247-253.
Bergius. The utilisation of wood for the production of foodstuffs, alcohol and glucose. Chemical society institution. Nov. 15, 1933.
Bergius. Winslow Notes on Bergius Process. 1937.
Bergius. Wood Sugar Plants at Mannheim-Rheinau & Regensburg. 1945.
Berndes, et al. The contribution of biomass in the future global energy supply: a review of 17 studies. Biomass and Bioenergy. 2003; 25:1-28.
Binder, et al. Mechanistic insights on the conversion of sugars into 5-hydroxymethylfurfural. Energy Environ. Sci., 2010; 3:765-771.
Bozell. The Use of Renewable Feedstocks for the Production of Chemicals and Materials—A Brief Overview of Concepts. National Renewable Energy Laboratory, 1617 Cole Boulevard, Golden, CO 80401. 2010.
Bridgwater, et al. Identification and market analysis of most promising added-value products to be co-produced with the fuels. Project No. 212831, Project end date: May 31, 2010; 1-132.
Brown, et al. Initial Market Assessment for Small-Scale Biomass-Based CHP, Prepared under Task No. WF6N.1050. National Renewable Energy Laboratory. Jan. 2008.
Brown. Determination of Dry Substance in Beet Sugar Juices, A Precision Method. Industrial and Engineering chemistry. Jul. 1924; 16(7):746-748.
Brummer, et al. Understanding Carbohydrate Analysis. Chapter 2. Copyright 2005 by Taylor & Francis Group, LLC.
Bunker. The Wartime Production of Food Yeast in Germany. 2010.
Burchell, et al. The development of novel activated carbon composites. 17th Annual Conference on Fossil Energy Materials, Wyndham Baltimore Inner Harbor Hotel, Baltimore, Maryland, Apr. 22-24, 2003.
Byrne. Expression, purification and crystallisation of membrane proteins. 2011.
Campa et al. Capillary Electrophoresis of Neutral Carbohydrates. Methods in molecular biology.2008; 384:247-305.
Campa et al. Capillary electrophoresis of sugar acids. Methods in molecular biology. 2008; 384: 307-355.
Campbell,et al. The Saccharification of Wood by the Bergius process at Suddeutschen Holzversucherung Werke A.G.

(56) References Cited

OTHER PUBLICATIONS

Regensburg. Report on visit to Suddeutschen Holzversucherung Werke A.G. Regensburg.CIOS trip No. 764, this target was visited on Aug. 9, 1945.
Campos. Calculations of VLE in electrolytes systems using chemical theory: aqueous acis chloridric system. 2nd Mercosur Congress on Chemical Engineering; 4th Mercosur Congress on Process Systems Engineering. 2008.
Cardona, et al. Production of bioethanol from sugarcane bagasse: Status and perspectives. Bioresource Technology. 2010; 101:4754-4766.
Carole, et al. Opportunities in the Industrial Biobased Products Industry. Applied Biochemistry and Biotechnology. 2004; 113-116:871-88.
Carr. The Biobased Revolution: How Biotechnology and Policy Are Changing the Way Materials Are Made. ASC Fall Convention & Expo. Oct. 11, 2005.
Carvalho, et al. Comparison of different procedures for the detoxification of eucalyptus hemicellulosic hydrolysate for use in fermentative processes. J Chem Technol Biotechnol 2006; 81:152-157.
Cayle, et al. The application of Mathews' Formula in Enzymatic Starch Conversions. Mar. 1966; 43:237-244.
Chaow-U-Thai et al. Removal of ash from sugarcane leaves and tops. International Journal of Biosciences.2012; 2(5): 12-17.
Cheng et al. A novel method to prepare L-arabinose from xylose mother liquor by yeast-mediated biopurification. Microbial cell factories.2011; 10 (43): 1-11.
Claricone Clarifiers and FiltraCone treatment plants. CB&I. Accessed Nov. 30, 2011.
Cole. XCV. The determination of reducing sugars by titration of ferricyanide. Biochem. 1933 xxvii, pp. 723-726.
Coma, et al. alpha-Glucosidase and N-Acetyl-p-o-glucosaminidase Isoenzymes in Serum. Clin. Chem. 1992; 38(2):223-226.
Cui. Structural Analysis of Polysaccharides. Chapter 3. Copyright 2005 by Taylor & Francis Group, LLC.
Curtis, et al. Equilibria in furfural-water systems under increased pressure and the influence of added salts upon the mutual solubilities of furfural and water. Aus. J. Sci. Res; 1948; 1(2): 213-235.
Delgado, et al. Sugar processing and by-products of the sugar industry. FAO Agricultural Services Bulletin 144. Rome, 2001.
Demirbas. Furfural Production from Fruit Shells by Acid-Catalyzed Hydrolysis, Energy Sources, Part A: Recovery, Utilization, and Environmental Effects. 2006; 28(2):157-165.
Demirbas. Products from lignocellulosic materials via degradation processes. Energy Sources, Part A. 2008; 30:27-37.
Dever, et al. Partial Chemical Characterization of Corn Root Cell Walls. Plant Physiol 43, 50-56, 1968.
Dipardo. Outlook for Biomass Ethanol Production and Demand. Energy Information Administration. 2008; 1-14.
Dyadic. AlternaFuel® 200P, Product #326, (For considerations in biomass saccharification applications). 2010.
Dyadic. Enzyme Development for Fuel Ethanol Production from Pre-treated Biomass, Technical Report May 2010, Saccharification I.D: Sacc 05.17.10.
Eyal, et al. Extraction of Strong Mineral Acids by Organic Acid-Base Couples. Ind. Eng. Chem. Process Des. Dev. 1982, 21, 334-337.
Eyal, et al. pH dependence of carboxylicand mineral acid extraction by amine-based extractants: effects of pKa, Amine Basicity, and diluent properties. Ind. Eng. Chem. Res. 1995; 34:1789-1798.
Eyal, et al. Recovery and concentration of strong mineral acids from dilute solutions through LLX.I: review of parameters for adjusting extractant propert and analysis of process options. Solvent Extraction and ion exchange. 1991; 9(2):195-210.
Eyal, et al. Sulfuric acid recovery through solvent aided decomposition of ammonium sulfate. Solvent Extraction and ion exchange. 1986; 44:803-821.
Fahim, et al. Liquid-Liquid Equilibria of the Ternary System Water + Acetic Acid + 1-Hexanol. J. Chem. Eng. Data. 1997; 42:183-186.
Foran, et al. Beyond 2025: Transitions to the biomass-alcohol economy using ethanol and methanol. Working Paper Series 99/07. Dec. 1999.
Foxit. Chemicals partition in wood. Mar. 2011.
Galego, et al. Mechanism of the thermal resinification of pure furfural . Revista CENIC, Ciencias Fisicas. 1975; 6(1):163-180. Abstract only.
Gamez et al. Study of the hydrolysis of sugar cane bagasse using phosphoric acid. Journal of Food Engineering.2006; 74: 78-88.
Georgieva et al. Enzymatic hydrolysis and ethanol fermentation of high dry matter wet-exploded wheat straw at low enzyme loading. Applied biochemistry and biotechnology; 2008; 148; 35-44.
Georgopoulos, et al. Thermoplastic polymers reinforced with fibrous agricultural residues. 2009.
Goldstein. Potential for Converting Wood into Plastics, Chemicals from wood may regain importance as the cost of petroleum continues to rise. Science, Sep. 12, 1975; 189(4206):847-852.
Gray, et al. Sugar Monomer and Oligomer Solubility, Data and Predictions for Application to Biomass Hydrolysis. Applied Biochemistry and Biotechnology. 2003; 105-108:179-193.
Grethlein, et al. The Cost of Ethanol Production from Lignocellulosic Biomass—A Comparison of Selected Alternative Processes. USDA. Specific Cooperative Agreement No. 58-1935-2-050. Apr. 30, 1993.
Griffith, et al. Low cost carbon fiber for transportation application. USDE. 2003.
Hagglund. The Decomposition of Wood by Acids wood Saccharification. Chemistry of Wood. New York: Academic Press, 1951. 631. Chapter IV. 390-413.
Hagglund. Wood Saccharification. A Modified Rheinau Process. 2011.
Hall. Polyhydric alcohol from wood. US Department of Agriculture, Forest Service, Forest Products Laboratory , Madison, Wisconsin. No. 1984. Jul. 1954.
Hallac, et al. Biomass Characterization of Buddleja davidii: A Potential Feedstock for Biofuel Production. J. Agric. Food Chem. 2009; 57(4):1275-1281.
Hamelinck, et al. Ethanol from lignocellulosic biomass: techno-economic performance in short-, middle- and long-term. Biomass and Bioenergy. 2005; 28:384-410.
Hamelinck, et al. Production of advanced biofuels. International Sugar Journal. 2006; 108(1287):168-175.
Han, et al. Optimizing lignocellulosic feedstock for improved biofuel productivity and processing. Biofuels, Bioprod. Bioref. 2007; 1:135-146.
Harada, et al. Formation of Isoamylase by Pseudomonas. Applied Microbiology. Oct. 1968; 16(10):1439-1444.
Harris, et al. Hydrolysis of wood cellulose with hydrochloric acid and sulfur dioxide and the decomposition of its hydrolytic products. Journal of Physical and Colloid Chemistry. (1949), 53:344-51. Abstract only.
Harris, et al. The Madison Wood-Sugar Process. US Dept. of Agriculture. Jun. 1946; 1-21.
Harris. Derived products and chemical utilization of wood waste. Forest Products Laboratory; Forest Service US Department of Agriculture; Rept. No. R1666-10. Jun. 1949.
Hasegawa, et al. New Pretreatment Methods Combining a Hot Water Treatment and Water/Acetone Extraction for Thermo-Chemical Conversion of Biomass. Energy & Fuels. 2004; 18:755-760.
Hayes, et al. The Biofine Process: Production of Levulinic Acid, Furfural and Formic Acid from Lignocellulosic Feedstocks. Biorefinery (8b). 2011.
Held. Catalytic conversion of renewable plant sugars to fungible liquid hydrocarbon fuels using the bioforming process. TAPPI IBBC session 3. Virent Energy systems. Oct. 15, 2009.
Herty Advanced Materials Development Center. HCl Clean Tech Composite Sample—Extracted Wood Sample. 2010.
Hinz, et al. Hemicellulase production in Chrysosporium lucknowense C1. Journal of Cereal Science. 2009; 50(3):318-323. doi:10.1016/j.jcs.2009.07.005.
Hirst, et al. CCCLXXXII.—The action of highly concentrated hydrochloric acid on cellulose and on some derivatives of glucose and of xylose. 1923; 3226-3235.

(56) References Cited

OTHER PUBLICATIONS

Hodge. Chemistry of Browning Reactions in Model Systems. Agricultural and Food Chemistry. Oct. 14, 1953; 1(15):928-943.
Holmen. Direct conversion of methane to fuels and chemicals. Catalysts Today. 2009; 142:2-8.
Hou-Rui, et al. Novel Isolates for Biological Detoxification of Lignocellulosic Hydrolysate. Appl Biochem Biotechnol 2009; 152:199-212.
Hu, et al. Chemical profiles of switchgrass. Bioresource Technology. 2010; 101:3253-3257.
Huber, et al. Synthesis of Transportation Fuels from Biomass: Chemistry, Catalysts, and Engineering. Chemical Reviews. Published on Web Jun. 27, 2006 p. EST: 54.3, 10.1021/cr068360d.
Huber. Breaking the Chemical and Engineering Barriers to Lignocellulosic Biofuels: Next Generation. Based on the: Jun. 25-26, 2007 ,Workshop, Washington D.C.
Hunag, et al. A review of separation technologies in current and future biorefineries. Separation and Purification Technology. 2008; 62:1-21.
Ibrahim, et al. Comparison of alkaline pulping with steam explosion for glucose production from rice straw. Carbohydrate Polymers. 2011; 83:720-726.
International search report and written opinion dated Feb. 15, 2013 for PCT/US2012/059542.
Iranmahboob, et al. Optimizing acid-hydrolysis: a critical step for production of ethanol from mixed wood chips. Biomass and Bioenergy. 2002; 22:401-404.
Ismagilov, et al. Direct conversion of methane on Mo/ZSM-5 catalysts to produce benzene and hydrogen: achievements and perspectives. Energy and Environmental Science. 2008; 1:526-541.
IsoClear 42% high fructose 80% solids corn syrup. Technical product information. Cargill. Updated Aug. 14, 2012.
Itzkowitz. Biodiesel from sugars. 2011.
Izydorczyk, et al. Polysaccharide Gums: Structures, Functional Properties, and Applications. Chapter 6. Copyright 2005 by Taylor & Francis Group, LLC.
Izydorczyk. Understanding the Chemistry of Food Carbohydrates. Chapter 1. Copyright 2005 by Taylor & Francis Group, LLC.
Jacobsen, et al. Xylose Monomer and Oligomer Yields for Uncatalyzed Hydrolysis of Sugarcane Bagasse Hemicellulose at Varying Solids Concentration, Industrial & Engineering Chemistry Research, 2002, 41, 1454-1461.
Johnson. Effects of Dilute Acid Hydrolyzate Components on Glucose Degradation. National Bioenergy Center, NREL, 1617 Cole Blvd., Golden, Colorado 80401, USA. 2011.
Kadam, et al. Generating Process and Economic Data Needed for Preliminary Design of PureVision Biorefineries. DOE Project No. DD-FG36-05GO85004, Final Nonproprietary Technical Report. Dec. 28, 2007.
Kaewwongsa, et al. Intestinal digestibility of the residual components of cassava pulp solid state fermentation by *Saccharomyces cerevisiae*. Suranaree J. Sci. Technol. 2009; 16(4):291-296.
Kamm, et al. Chemical and biochemical generation of carbohydrates from lignocellulose-feedstock (*Lupinus nootkatensis*)—quantification of glucose. Chemosphere. 2006; 62:97-105.
Kamm, et al. Definition and technical status of Biorefineries. BioreFuture 2008, Tuesday Feb. 12, 2008, Brussels.
Khan, et al. Kinetic Study on Palm Oil Waste Decomposition. Biofuel's Engineering Process Technology. 2011. Chapter 22, pp. 523-536.
Kim, et al. Continuous Countercurrent Extraction of Hemicellulose from Pretreated Wood Residues. Applied Biochemistry and Biotechnology. 2001; 91-93:253-267.
Kim, et al. Enzyme hydrolysis and ethanol fermentaion of liquid hot water and AFEX pretreated distillers' grains at high-solid loadings. Bio. Tech. 2008; 99:5206-5215.
Kimberley, et al. A colorimetric method for the quantitation of galacturonic acid. Applied biochemistry and biotechnology. 1993; 43:51-54.
Kinders, et al. Saccharification of HCl-treated substrate provided by HCL-Cleantech, Technical Report, Mar. 2010. Dyadic International Inc. // Confidential and Proprietary Information.
Kjellstrand, et al. Development of toxic degradation products during heat sterilization of glucose-containing fluids for peritoneal dialysis: influence of time and temperature. Perit Dial Int. 1995;15(1):26-32.
Kribble, et al. The Electromotive Force Measurements of Hydrochloric Acid Solutions with and without Sucrose and their Relation to the Rate of Sucrose Hydrolysis. Jan. 1935; 57:19-22.
Kucuk, et al. Biomass Conversion Processes. Energy Conyers. Mgmt. 1997; 38(2):151-165.
Kumar, et al. Effect of Enzyme Supplementation at Moderate Cellulase Loadings on Initial Glucose and Xylose Release From Corn Stover Solids Pretreated by Leading Technologies. Biotechnology and Bioengineering. Feb. 1, 2009; 102(2):457-567.
Kumar, et al. Methods for Pretreatment of Lignocellulosic Biomass for Efficient Hydrolysis and Biofuel Production. Ind. Eng. Chem. Res. 2009; 48:3713-3729.
Lam, et al. Kinetic Modeling of Pseudolignin Formation in Steam Exploded Woody Biomass. 2011.
Lange, et al. Lignocellulose conversion: an introduction to chemistry, process and economics. Biofuels, Bioprod. Bioref. 2007; 1:39-48.
Lavarack, et al. The acid hydrolysis of sugarcane bagasse hemicellulose to produce xylose, arabinose, glucose and other products. Biomass and Bioenergy. 2002; 23:367-380.
Lee, et al. Dilute-Acid Hydrolysis of Lignocellulosic Biomass. Advances in Biochemical Engineering/ Biotechnology. 1999; 65:93-115.
Leonard, et al. Fermentation of wood sugars to ethyl alcohol. US Department of Agriculture, Forest Service, Forest Products Laboratory, Madison, Wisconsin. No. R1466. Dec. 1944.
Leshchuk, et al. Penetration of concentrated hydrochloric acid into the pores of wood particles and the formation of hydrolyzates within the particles. Sbornik Trudov. Gosudarstvennyi Nauchno-issledovatel'skii Institut Gidroliznoi i Sul'fitno-spirtovoi Promyshlennosti (1966), 15 156-67. CODEN: SGSSAC. Abstract only.
Li, et al. Acidolysis of Wood in Ionic Liquids. Ind. Eng. Chem. Res. 2010; 49(7):3126-3136.
Li, et al. Interaction of Supercritical Fluids with Lignocellulosic Materials. Ind. Eng. Chem. Res. 1988; 27:1301-1312.
Lin, et al. Ethanol fermentation from biomass resources: current state and prospects. Appl Microbiol Biotechnol. 2006; 69:627-642.
Liu. Understanding Starches and Their Role in Foods. Chapter 7. Copyright 2005 by Taylor & Francis Group, LLC.
Lora. GreenValue—Technologies and Products. GreenValueEnterprises LLC, Media, PA, USA. 2011.
Lora. Non-Wood Biorefinery Developments Outside North America. 2011.
Lu, et al. Hydrolysis of Japanese beech by batch and semi-flow water under subcritical temperatures and pressures. Biomass and Bioenergy, Feb. 2010, pp. 1089-1097.
Lynd, et al. Strategic Biorefinery Analysis: Analysis of Biorefineries, Jan. 24, 2002-Jul. 1, 2002. Subcontract Report, NREL/SR-510-35578, Jan. 10, 2005.
Mabee, et al. Updates on Softwood-to-Ethanol Process Development. Applied Biochemistry and Biotechnology, 2006;129-132:55-70.
Mai, et al. Biotechnology in the wood industry. Appl Microbiol Biotechnol; 2004; 63:477-494.
Marchal, et al. Conversion into acetone and butanol of lignocellulosic substrates pretreated by steam explosion. Biotechno!ogy Letters. 1986; 8(5):365-370.
Marker, et al. Optical properties of glucose. 2009.
Mascal, et al. Direct, High Yield Conversion of Cellulose into Biofuel. Angew. Chem. Int. Ed. 2008; 7:7924-7926.
Mascal, et al. High-Yield Chemical Conversion of Biomass into Biofuels and Value added Products. Clean Technology 2010, www.ct-si.org, ISBN 978-1-4398-3419-0. 124-127.
Mascal, et al. Towards the Efficient, Total Glycan Utilization of Biomass. ChemSusChem. 2009; 2:423-426.

(56) References Cited

OTHER PUBLICATIONS

Mcaloon, et al. Determining the Cost of Producing Ethanol from Corn Starch and Lignocellulosic Feedstocks. National Renewable Energy Laboratory, Contract No. DE-AC36-99-GO10337, NREL/TP-580-28893. Prepared under Task No. BFP1.7110. Oct. 2000.
McKenzie, et al. Levulinic acid. Organic Syntheses, Coll. vol. 1, p. 335 (1941); vol. 9, p. 50 (1929). Apr. 29, 2010.
Mielenz. Ethanol production from biomass: technology and commercialization status. Current Opinion in Microbiology. 2001; 4:324-329.
Mikkola, et al. Hydrolytic decomposition of glycosides in aqueous acids. ARKIVOC 2009 (iii) 39-53.
Miljkovic. Carbohydrates, Synthesis, Mechanisms, and Stereoelectronic Effects. Springer Science+Business Media, LLC 2009.
Minifie. Chocolate, Cocoa, and Confectionery. Science and Technology. An Aspen Publication. 3rd Ed. 1989.
Moelwyn-Hughes. The kinetics of the hydrolysis of certain glucosides, part 11: trehalose, umethylglucoside and tetramethyl-a-amethyglucoside. Nov. 23, 1928; 81-92.
Mythili, et al. Synthesis, mechanical, thermal and chemical properties of polyurethanes based on cardanol. Bull. Mater. Sci. Jun. 2004 ;27(3):235-241.
Nikam et al. Density and Viscosity Studies of Glucose and Fructose Solutions in Aqueous and in NH4CL. Journal of Molecular Liquids; 2000; 87; 97-105.
Novozymes. The key to the first commercially viable enzymes for cellulosic ethanol. 2010. www.bioenergy.novozymes.com.
Nrel. Enzyme Sugar-Ethanol Platform Project. National Renewable Energy Laboratory , Operated for the U.S. Department of Energy by Midwest Research Institute • Battelle • Bechtel. 2010.
Nystrand. Feasibility of lignocellulose as feedstock for biological production of super absorbent polymers. Department of Physics, Chemistry and Biology Master's Thesis; Linköping University Department of Physics, Chemistry and Biology 581 83 Linköping. Oct. 2010.
Office action dated Dec. 4, 2014 for U.S. Appl. No. 14/385,142.
Office action dated Dec. 4, 2014 for U.S. Appl. No. 14/485,617.
Office action dated Dec. 4, 2014 for U.S. Appl. No. 14/512,321.
Olsson, et al. Fermentation of lignocellulosic hydrolysates for ethanol production. Enzyme and Microbial Technology. 1996; 18:312-331.
Onda et al. Selective Hydrolysis of Cellulose and Polysaccharides into Sugars by Catalytic Hydrothermal Method Using Sulfonated Activated-carbon. Journal of Japan Petroleum Institue.2012; 55(2): 73-86.
Ong. Conversion of lignocellulosic biomass to fuel ethanol—a brief review. The planter koala lumpur. 2004; 80(941):517-524.
Palmqvist, et al. Fermentation of lignocellulosic hydrolysates. II: inhibitors and mechanisms of inhibition. Bioresource Technology. 2000; 74:25-33.
Pan, et al. Biorefining of Softwoods Using Ethanol Organosolv Pulping: Preliminary Evaluation of Process Streams for Manufacture of Fuel-Grade Ethanol and Co-Products. Biotechnology and bioengineering. May 20, 2005; 90(4).
Pan, et. al. Pretreatment of Lodgepole Pine Killed by Mountain Pine Beetle Using the Ethanol Organosolv Process: Fractionation and Process Optimization. Ind. Eng. Chem. Res. 2007;46: 2609-2617.
Papadopoulous, et al. Behavior of sweetgum wood xylan and lignin during hydrolysis with concentrated hydrochloric acid at moderate temperatures. Dep. Wood Pap. Sci., North Carolina State Univ., Raleigh, NC, USA. Journal of Applied Polymer Science: Applied Polymer Symposium (1983), 37(Proc. Cellul. Conf., 9th, 1982, Part 2), 631-40. CODEN: JPSSDD ISSN: 0271-9460. Abstract only.
Paszner, et al. High-yield Organosolv process for conversion of cellulosic biomass to ethanol. Fac. For., Dep. Harvest. Wood Sci., Vancouver, BC, Can. Energy from Biomass and Wastes (1989), 12 1297-318. CODEN: EBWADU ISSN: 0277-7851. Abstract only.
Patel, et al. Medium and long-term Opportunities and Risks of the Biotechnological Production of Bulk Chemicals from Renewable Resources—The Potential of White Biotechnology The BREW project. Utrecht University. Sep. 2006. www.chem.uu.nl/nws.
Pazur. Reversibility of enzymatic transglucosylation reactions. Received for publication, Jan. 17, 1955, pp. 531-538.
Perlack, et al. Biomass as feedstock for a bioenergy and bioproducts industry: the technical feasibility of a billion-ton annual supply. U.S. Department of Energy, under contract DE-AC05-00OR22725. Apr. 2005.
Pessoa JR, et al. Acid hydrolysis of hemicellulose from sugarcane bagasse. Braz. J. Chem. Eng. vol. 14 No. 3 São Paulo Sep. 1997.
Philip, et al. Review Polyhydroxyalkanoates: biodegradable polymers with a range of applications. J Chem Technol Biotechnol. 2007; 82:233-247.
Phillips, et al. Thermochemical Ethanol via Indirect Gasification and Mixed Alcohol Synthesis of Lignocellulosic Biomass. National Renewable Energy Laboratory, Technical Report NREL/TP-510-41168. Apr. 2007.
Phillips. Technoeconomic Analysis of a Lignocellulosic Biomass Indirect Gasification Process to Make Ethanol. Ind. Eng. Chem. Res. 2007; 46:8887-8897.
Pierce. Instruction Acylation Derivatization Reagents. Pierce, Rockford, IL 61105, US. 2010.
Ping, et al. Evaluation of grape stalks as a bioresource. Industrial Crops and Products. 2011; 33:200-204.
Polymer Science. Making Polyurethane. Polymer Science Learning Center, Department of Polymer Science the University of Southern Mississippi. 2005.
Prater, et al. Determination of Sulfur Dioxide in Dehydrated Foods. Industrial and engineering chemistry. Mar. 1944; 16(3):153-157.
Priefert, et al. Biotechnological production of vanillin. Appl Microbiol Biotechnol. 2001; 56:296-314. Abstract only.
Qian, et al. Acidic Sugar Degradation Pathways An Ab Initio Molecular Dynamics Study. Applied Biochemistry and Biotechnology. 2005;121-124:989-997.
Rabinovich. Wood hydrolysis industry in the Soviet Union and Russia: a mini-review. Cellulose Chem. Technol.2010; 44(4-6):173-186.
Radiotis, et al. Optimizing Production of Xylose and Xylooligomers from Wood Chips. 3rd NWBC, Stockholm, Sweden Mar. 23, 2011.
Ragauskas, et al. From wood to fuels Integrating biofuels and pulp production. Industrial biotechnology. 2006; 2(1):55-65.
Ragauskas, et al. The Path Forward for Biofuels and Biomaterials. Science. Jan. 26, 2006; 311:484-489.
Raz. Weyland bioethanol report. 2010.
Ritcey et al. Development of Industrial Solvent Extraction Processes. (Report) Gordon M. Ritcey & Associates, Inc; Nepean, Ontario, Canada.2004.
Robbins, et al. Liquid-Liquid Extraction Operations and Equipment. Sec. 15. 2009.
Rockwood, et al. Energy Product Options for Eucalyptus Species Grown as Short Rotation Woody Crops. Int. J. Mol. Sci. 2008; 9:1361-1378; DOI: 10.3390/ijms9081361.
Rondinini, et al. Reference value standards and primary standards for pH measurements in Organic Solvents and Water + Organic Solvent Mixtures of Moderate to High Permittivities. Pure & Appl. Chem. 1987; 59(11):1549-1560.
Rovio, et al. Determination of monosaccharide composition in plant fiber materials by capillary zone electrophoresis. Journal of Chromatography A. 2008; 1185:139-144.
Rovio, et al. Determination of neutral carbohydrates by CZE with direct UV detection. Electrophoresis. 2007; 28:3129-3135.
Rozmarin, et al. Fermentative evaluation of prehydrolyzates from chemical cellulose manufacturing. II. Study on some factors affecting the inversion process. Rom. Revista Padurilor-Industria Lemnului-Celuloza si Hirtie: Celuloza si Hirtie (1977), 26(4), 158-62. CODEN: RPLHDX ISSN: 0258-2287. Abstract only.
Rumbold. Selection of production hosts for real-life feedstock utilization. TNO Kwaliteit van Leven, Oct. 20, 2007.
Saari et al. Adsorption Equilibria of Arabinose, Fructose, Galactose, Rhamnose , Sucrose , and Xylose on Ion-Exchange Resins. J. Chem. Eng.; 2010; 55; 3462-3467.
Saeman. Kinetics of the hydrolysis of wood and of the decomposition of sugars in dilute acid at high tempratures. USDA. Sep. 1944.

(56) References Cited

OTHER PUBLICATIONS

Saha, et al. Dilute Acid Pretreatment, Enzymatic Saccharification, and Fermentation of Rice Hulls to Ethanol. Biotechnol. Prog. 2005; 21:816-822.
Saltberg, et al. Removal of metal ions from wood chips during acidic leaching 1:Comparison between Scandinavian softwood, birch and eucalyptus. Nordic Pulp and Paper Research J. 2006; 21(4):507-512.
Saltberg, et al. Removal of metal ions from wood chips during acidic leaching 2: Modeling leaching of calcium ions from softwood chips. Nordic Pulp and Paper Research J. 2006; 21(4):513-519.
Sanchez, et al. Structural analysis of acid catalysed furfuraldehyde resins by thermal degradation techniques. Eur. Polym. J. 1994; 30(1):43-50.
Sanchez, et al. Trends in biotechnological production of fuel ethanol from different feedstocks. Bioresource Technology. 2008; 99:5270-5295.
Sanders, et al. Shuttle hydrochloric acid process for the preparation of oligosaccharides containing products from wood. Comm. Eur. Communities, [Rep.] EUR (1987), (EUR 11084, Degrad. Lignocellul. Ruminants Ind. Processes), 97-101. CODEN: CECED9 ISSN: 0303-755X. Abstract only.
Sasaki, et al. Cellulose hydrolysis in subcritical and supercritical water. J. of Supercritical Fluids. 1998; 13:261-268.
Sasaki, et al. Dissolution and Hydrolysis of Cellulose in Subcritical and Supercritical Water. Ind. Eng. Chem. Res. 2000, pp. 2883-2890.
Sassner, et al. Techno-economic evaluation of bioethanol production from three different lignocellulosic materials. Biomass and bioenergy. 2008; 32:422-430.
Satin Sweet® 65% High Maltose Corn Syrup. Cargill foods. www.cargillfoods.com Updated Aug. 12, 2014.
Sato, et al. Determination of monosaccharides derivatized with 2-aminobenzoic Acid by capillary electrophoresis. Ana. BioChem. 1997; 251: 119-121.
Schaefer. Bio-Based opportunities in chemicals & energy. Novozymes. London, UBS. Nov. 17, 2010.
Schoenemann. The New Rheinau Wood Saccharification Process. Institute of Chemical Technology. Jul. 27, 1953; 1-49.
Schuchardt et al. Hydrolysis of sugar cane bagasse with hydrochloric acid, promoted by metallic cations. Journal of Chemical Technology & Biotechnology. 1986; 36:329-334.
Scurfield, et al. Amino-Acid Composition of Wood Proteins. J. Experimental Botany. 1970; 21(6):857-68.
Sharkov. Production of Polyhydric Alcohols from Wood Polysaccharides. Angew. Chem. internat. Edit. 1963; 2(8):405-492.
Sheehan, et al. Energy and Environmental Aspects of Using Corn Stover for Fuel Ethanol. Journal of Industrial Ecology. 2004; 7(3-4):117-146.
Shen, et al. Product overview and market projection of emerging bio-based plastics, Utrecht University. PRO-BIP 2009.
Shimizu, et al. Integrated process for total utilization of wood components by steam-explosion pretreatment. Biomass and bioenergy. 1998; 14(3):195-203.
Sidiras, et al. Simulation of acid-catalysed organosolv fractionation of wheat straw. Bioresource Technology. 2004; 94:91-98.
Sigma. Enzymatic Assay of α-GLUCOSIDASE. Sigma quality control test procedure. Sigma Product information, Revised: Aug. 9, 1996.
Sigma. Enzymes and Reagents for Alternative Energy. Sigma-Aldrich. Biofiles. 2010; 5(5).
Singh, et al. Visualization of Biomass Solubilization and Cellulose Regeneration During Ionic Liquid Pretreatment of Switchgrass. Biotechnology and Bioengineering. Sep. 1, 2009; 104(1):68-75.
Sluiter, et al. Determination of Ash in Biomass, Laboratory Analytical Procedure (LAP), Issue Date: Jul. 17, 2005. Technical Report, NREL/TP-510-42622, Jan. 1, 2008.
Sluiter, et al. Determination of Sugars, Byproducts, and Degradation Products in Liquid Fraction Process Samples, Laboratory Analytical Procedure (LAP), Issue Date: Dec. 8, 2006. Technical Report, NREL/TP-510-42623, Jan. 1, 2008.
Sluiter, et al. Determination of Sugars, Byproducts, and Degradation Products in Liquid Fraction Process Samples. Laboratory Analytical Procedure (LAP), Contract No. DE-AC36-99-GO10337. Issue Date: Dec. 8, 2006.
Sluiter, et al. Determination of Total Solids in Biomass and Total Dissolved Solids in Liquid Process Samples, Laboratory Analytical Procedure (LAP), Issue Date: Mar. 31, 2008. Technical Report, NREL/TP-510-42621, Revised Mar. 2008.
So, et al. Economic Analysis of Selected Lignocellulose-to-Ethanol Conversion Technologies. Applied Biochemistry and Biotechnology. 1999; 77-79:633-640.
Soloman, et al. Grain and cellulosic ethanol: History, economics, and energy policy. Biomass and Bioenergy. 2007; 31:416-425.
Srinorakutara, et al. Approach of Cassava Waste Pretreatments for Fuel Ethanol Production in Thailand. 2010.
Srinorakutara, et al. Utilization of Waste from Cassava Starch Plant for Ethanol Production. The Joint International Conference on "Sustainable Energy and Environment (SEE)" Dec. 1-3, 2004, Hua Hin, Thailand. 344-349.
Steele. Recent breakthroughs in enzymes for biomass hydrolysis. Genecor. National Ethanol Conference, Feb. 23-25, 2009, San Antonio, Texas.
Suess. Interaction of organic compounds with calcium carbonate-I. Association phenomena and geochemical implications. Geochimia et Cosmochimic Acata. 1970; 34:157-168.
Sun, et al. Hydrolysis of lignocellulosic materials for ethanol production: a review. Bioresource Technology. 2002; 83:1-11.
Taherzadeh, et al. Pretreatment of Lignocellulosic Wastes to Improve Ethanol and Biogas Production: A Review. Int. J. Mol. Sci. 2008; 9:1621-1651; DOI: 10.3390/ijms9091621.
Thomsen. How 'green' are algae farms for biofuel production? Biofuels. 2010; 1(4):515-517.
Timell, et al. The acid hydrolysis of glycosides II. Effect of substituents at C-5. Canadian Journal of Chemistry. 1965; 43:2296-2305.
Trickett. Utilization of Baggase for the production of C5 and C6 sugars. MS Thesis; University of Natal, Durban, South Africa. 1982.
Urban, et al. Characterization of polymer-based monolithic capillary columns by inverse size-exclusion chromatography and mercury-intrusion porosimetry. Journal of Chromatography A. 2008; 1182:161-16.
Van Bramer. An Introduction to Mass Spectrometry. Widener University, Department of Chemistry, One University Place, Chester, PA 19013. 1998.
Van Dyke. Enzymatic Hydrolysis of Cellulose—A Kinetic Study. For the degree of Doctor of Science at the Massachusetts Institute of Technology, Sep. 1972.
Von Sivers, et al. A techno-economical comparison of three processes for the production of ethanol from pine. Bioresource Technology. 1995; 51:43-52.
Vulfson, et al. Glycosidases in organic solvents: I. Alkyl-fl-glucoside synthesis in a water-organic two-phase system. Enzyme Microb. Technol. Dec. 1990; 12:950-954.
Wang, et al. Molecular Characteristics of Kraft-AQ Pulping Lignin Fractionated by Sequential Organic Solvent Extraction. Int. J. Mol. Sci. 2010; 11:2988-3001.
Wang, et al. Understanding the Conformation of Polysaccharides. Chapter 5. Copyright 2005 by Taylor & Francis Group, LLC.
Wang, et al. Understanding the Physical Properties of Food Polysaccharides. Chapter 4. Copyright 2005 by Taylor & Francis Group, LLC.
Weingarten, et al. Kinetics of furfural production by dehydration of xylose in a biphasic reactor with microwave heating. Green Chem. 2010; 12:1423-1429.
Williams. Ethanol production potential and costs from lignocellulosic resources in California. 15th European Biomass Conference & Exhibition, May 7-11, 2007, Berlin, Germany.
Wilson, et al. Detection of tannins in modern and fossil barks and in plant residues by high-resolution solid-state $^{13}$C nuclear magnetic resonance. Org. Geochem. 1988; 12(6):539-546.
Winandy, et al. Wood-plastic composites using thermomechanical pulp made from oxalic acid-pretreated red pine chips. 7th Global

(56) References Cited

OTHER PUBLICATIONS

WPC and Natural Fibre Composites Congress and Exhibition, Jun. 18-19, 2008 in Kassel / Germany.
Woodbridge et al. Nitrocellulose from wood pulp. J. Ind.Eng. Chem. 1920; 12(4):380-384.
Wood-Ethanol Report. Environment Canada. 1999.
Wyman, et al. Comparative sugar recovery data from laboratory scale application of leading pretreatment technologies to corn stover. Bioresource Technology. 2005; 96: 2026-2032.
Wyman. Biomass ethanol: Technical Progress, Opportunities, and Commercial Challenges. Annu. Rev. Energy Environ. 1999; 24:189-226.
Wyman. Potential Synergies and Challenges in Refining Cellulosic Biomass to Fuels, Chemicals, and Power. Biotechnol. Prog. 2003; 19:254-262.
Wyman. Twenty Years of Trials, Tribulations, and Research Progress in Bioethanol Technology. Applied Biochemistry and Biotechnology. 2001; 91-93:5-21.
Wyman. What is (and is not) vital to advancing cellulosic ethanol. TRENDS in Biotechnology. 2007; 25(4):153-157.
Yusmawati, et al. Optical Properties and Sugar Content Determination of Commercial Carbonated Drinks using Surface Plasmon Resonance. American Journal of Applied Sciences. 2007; 4(1):01-04.
Zahedifar. Novel uses of lignin and hemicellulosic sugars from acidhyrolysed lignocellulosic materials. For the degree of Doctor of Philosophy, in the University of Aberdeen, Sep. 1996.
Zhang. Reviving the carbohydrate economy via multi-product lignocellulose biorefineries. J Ind Microbiol Biotechnol. 2008; 35:367-375.
Zhao, et al. Small-scale mashing procedure for predicting ethanol yield of sorghum grain. Journal of Cereal Science. 2009; 49:230-238.
Zinoviev, et al. Background Paper on biofuels Production Technologies. International Centere for Science and Hight Technology and UNIDO. Nov. 2007; 1-106.
Zorina, et al. Study of acid heterogeneous hydrolysis of pulp. USSR. Editor(s): Kiprianov, A. I. Khim Pererab. Drev. (1982), 35-8. Publisher: Leningr. Lesotekh. Akad., Leningrad, USSR CODEN: 49HIA6. Abstract only.
Cassales, et al. Optimization of soybean hull acid hydrolysis and its characterization as a potential substrate for bioprocessing. Biomass and Bioenergy. 2011; 35:4675-4683.
Corn sweetener guide. Corn sweetener refining with ion exchange resins. Purolite. Jan. 18, 2007. 60 pages.
DOWEX Ion exchange resins for HFCS deashing and polishing. Technical Manual. The Dow Chemical Company. Published Jun. 2002. 28 pages.
Reimann, et al. Element levels in birch and spruce wood ashes—green energy? Science of the Total environment. 2008; 393:191-197.
Sluiter, et al. Determination of Ash in Biomass Laboratory Analytical Procedure (LAP). Issued Jul. 17, 2005. Technical Report NREL/TP-510-42622. Jan. 2008. 8 pages.
Standard test method for ash in biomass. ASTM International. Designation E1755. Reapproved Oct. 9, 2015. 3 pages.
The use of DOWEX ion exchange resins in corn sweetener processing. The Dow Chemical Company. Published Jun. 2002. 12 pages.
U.S. Appl. No. 15/298,145, filed Oct. 19, 2016, Eyal et al.
Carvalheiro, et al. Hemicellulose biorefineries: a review on biomass pretreatments. Journal of Scientific & Industrial Research 2008; 849-864.
Kaparaju, et al. Bioethanol, biohydrogen and biogas production from wheat straw in a biorefinery concept. Bioresour Technol. May 2009;100(9):2562-8. doi: 10.1016/j.biortech.2008.11.011. Epub Jan. 8, 2009.
Office action dated Oct. 18, 2016 for U.S. Appl. No. 14/385,142.
Office action dated Oct. 18, 2016 for U.S. Appl. No. 14/730,118.

Zhang, et al. Ethanol production from paper sludge by simultaneous saccharification and co-fermentation using recombinant xylose-fermenting microorganisms Biotechnology and bioengineering. 2010; 107(2):235-244.
Agblevor, et al. Analysis of biomass sugars using a novel HPLC method. Appl Biochem Biotechnol. Mar. 2007;136(3):309-26.
Allosio-Ouarnier, et al. Application of High Performance Anion Exchange Chromatography to the Study of Carbohydrate Changes in Barley During Malting. Journal—Institute of Brewing 106(1):45-52. Jan. 2000.
Biology Online. "Oligosaccharide". Downloaded Mar. 27, 2017. 1 page.
Buranov, et al. Extraction and characterization of hemicelluloses from flax shives by different methods. Carbohydrate Polymers, vol. 79, No. 1, 2010 (pp. 17-25).
Chandel, et al. Detoxification of Lignocellulosic Hydrolysates for Improved Bioethanol Production. Biofuel Production—Recent Developments and Prospects. Sep. 1, 2011, pp. 225-246.
dictionary.com. "Oligosaccharide". Downloaded Mar. 27, 2017. 2 pages.
Encyclopaedia Britannica. Biochemistry. "Oligosaccharide". Downloaded Mar. 27, 2017. 1 page.
Ferrari, et al., Ethanol production from eucalyptus wood hemicellulose hydrolysate by pichia stipitis, 1992, biotech and bioengineering, 40:753-759.
Finney, Nathaniel. Essentials of Glycobiology. Carbohydrate Structure and Nomenclature. Lecture. Apr. 1, 2004. pp. 1-26.
Gullon, et al. Production of oligosaccharides and sugars from rye straw: a kinetic approach. Bioresource technology, 2010, 101(17), pp. 6676-6684.
Hanchar, et al. Separation of glucose and pentose sugars by selective enzyme hydrolysis of AFEX-treated corn fiber. Appl Biochem Biotechnol. Apr. 2007;137-140(1-12):313-25. doi: 10.1007/s12010-007-9061-3.
Heinonen, et al. Chromatographic recovery of monosaccharides for the production of bioethanol from wood. Ind. Eng. Chem. Res. 2010; 49:2907-2915.
Hu, et al. The direct conversion of xylan to lactic acid by lactobacillus brevis transformed with a xylanase gene. Green Chem., vol. 13(7), pp. 1729-1734 (2011).
Ioannidou et al. Direct determination of toxic trace metals in honey and sugars using inductively coupled plasma atomic emission spectrometry. Talanta, 65(1): 92-97 (2005).
Kunkes, et al. Catalytic conversion of biomass to monofunctional hydrocarbons and targeted liquid-fuel classes. Science. Oct. 17, 2008;322(5900):417-21. doi: 10.1126/science.1159210. Epub Sep. 18, 2008.
Martinez, et al. Detoxification of dilute acid hydrolysates of lignocellulose with lime. Biotechnology Progress, American Institute of Chemical Engineers, vol. 17, Jan. 1, 2001, pp. 287-293.
Medical Dictionary: thefreedictionary.com. "Oligosaccharide". Downloaded Mar. 27, 2017. 2 pages.
Michalka, Optimization of Sugar Consumption in the Fermentation of Temulose for Ethanol Production, 2007.
Miller-Ihli et al. Direct determination of lead in sugars using graphite furnace atomic absorption spectrometry. Atomic Spectroscopy, 14(4): 85-89 (1993).
Notice of Allowance dated Feb. 1, 2017 for U.S. Appl. No. 14/385,142.
nutrients review.com. "Oligosaccharides". Downloaded Mar. 27, 2017. 4 pages.
Office Action dated Jan. 26, 2017 for U.S. Appl. No. 14/730,118.
Office Action dated Mar. 31, 2017 for U.S. Appl. No. 15/298,145.
Oxford Dictionary. "Oligosaccharide". Downloaded Mar. 27, 2017. 1 page.
Pohl et al. Direct Determination of the Total Concentrations of Magnesium, Calcium, Manganese, and Iron in Addition to their Chemical and Physical Fractions in Dark Honeys. Anal. Lett., 44(13): 2265-2279 (2011).
Schenck. Glucose and Glucose-Containing Syrups. Ullmann's Encyclopedia of Industrial Chemistry, vol. 17, http://dx.doi.org/1 0.1002%2F14356007.a12_457.pub2, 2006 (pp. 45-66).

(56) References Cited

OTHER PUBLICATIONS

Sevcik, et al. Rapid analysis of carbohydrates in aqueous extracts and hydrolysates of biomass using a carbonate-modified anion-exchange column. J Chromatogr A. Mar. 4, 2011;1218(9):1236-43. doi: 10.1016/j.chroma.2011.01.002. Epub Jan. 11, 2011.
Sun, et al. Characterization and esterification of hemicelluloses from rye straw. Journal of Agricultural and Food Chemistry. 2000, 48(4), pp. 1247-1252.
Terol et al. High-Temperature Liquid Chromatography Inductively Coupled Plasma Atomic Emission Spectrometry hyphenation for the combined organic and inorganic analysis of foodstuffs. J. Chromatography, 1217(40): 6195-6202 (2010).
Vassilev, et al. An overview of the chemical composition of biomass. Fuel, vol. 89, Issue 5, May 2010, pp. 913-933. Available online Nov. 10, 2009.
Veres et al. Studies on matrix effects in the determination of the metal content of sugar complexes by atomic absorption spectrometry. Magyar Kemiai Folyoirat, 93(5): 199-204 (1987).
Winter, et al. NO and N2O formation during the combustion of wood, straw, malt waste and peat. Bioresource Technology. vol. 70, Issue 1, Oct. 1999, pp. 39-49.
Wu et al. Determination of trace calcium in glucose by Zeeman flame atomic absorption spectrometry. Guangdong Weiliang Yuansu Kexue, 14(3): 58-60 (2007).
Zhang, et al. Cellodextrin preparation by mixed-acid hydrolysis and chromatographic separation. Analytical Biochemistry, 322(2), 2003 (pp. 225-232).
Zhao, et al. Fermentable hexose production from corn stalks and wheat straw with combined supercritical and subcritical hydrothermal technology. Bioscience Technology, vol. 100, Jul. 18, 2009, pp. 5884-5889.
Zhao, et al., Organosolv pretreatment of lignocellulosic biomass for enzymatic hydrolysis, Appl Microbiol Biotechnol (2009) 82:815-827.
Zhao, et al. Supercritical hydrolysis of cellulose for oligosaccharide production in combined technology. Chem. Eng. J. 2009; 150:411-417.
Górecka, et al. The application of ICP-MS and ICP-OES in determination of micronutrients in wood ashes used as soil conditioners. Talanta. Dec. 15, 2006;70(5):950-6.
Neureiter et al. Dilute-acid hydrolysis of sugarcane bagasse at varying conditions. Applied Biochemistry and Biotechnology. Mar. 2002, vol. 98, Issue 1-9, pp. 49-58.
Co-pending U.S. Appl. No. 15/573,801, filed Nov. 13, 2017.
Notice of Allowance dated Nov. 1, 2017 for U.S. Appl. No. 14/730,118.

\* cited by examiner

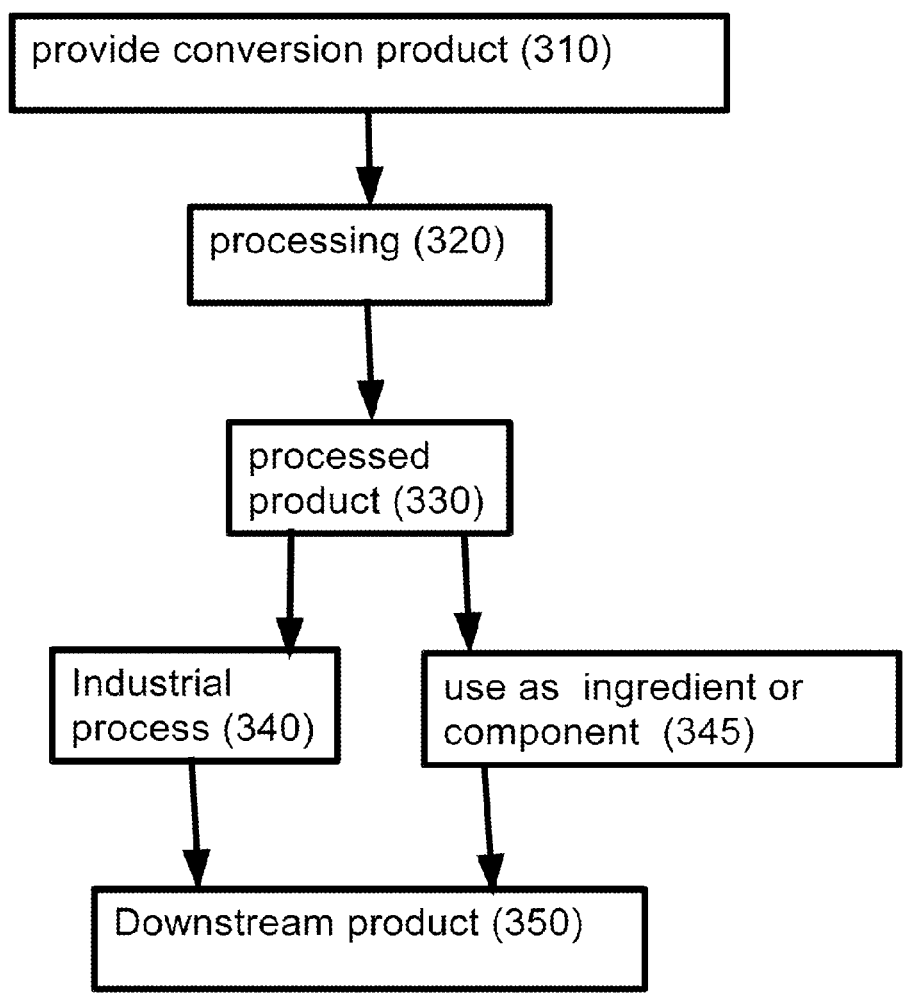

SUGAR COMPOSITIONS

RELATED APPLICATIONS

The present application is a Continuation of U.S. patent application Ser. No. 14/512,321, filed Oct. 10, 2014, now abandoned, which is a Continuation of U.S. patent application Ser. No. 14/385,142, now U.S. Pat. No. 9,617,608, filed Sep. 12, 2014, which claims the benefit of International Application No. PCT/2012/059542, filed on Oct. 10, 2012, which claims priority to U.S. Provisional Patent Application No. 61/545,389, filed Oct. 10, 2011, entitled "SUGAR COMPOSITIONS AND USES THEREOF," each of which applications are incorporated herein by reference in theft entirety.

FIELD OF THE INVENTION

This invention relates to sugar compositions.

BACKGROUND OF THE INVENTION

The increasing cost of fossil fuels has created a demand for alternative energy sources. This demand is reflected in the Renewable Fuel Standard (RFS), established by the U.S. Environmental Protection Agency (EPA) under the Energy Independence and Security Act of 2007. RFS has set standards to increase the volume of renewable fuel required to be blended into gasoline from 9 billion gallons in 2008 to 36 billion gallons by 2022, composed of 15 billion gallons of renewable fuel and 21 billion gallons of advanced bio-fuels (16 billion gallons cellulosic bio-fuels).

One theoretically feasible way to produce alternative fuels is by chemical conversion of carbon containing substrates using non-enzymatic catalysts. In practice, development of this technology has revealed a variety of technical problems including, but not limited to, fouling or poisoning of catalysts, unacceptably low yields of conversion product and requirements for reaction conditions which make the conversion process industrially unattractive.

SUMMARY OF THE INVENTION

A broad aspect of the invention relates to sugar compositions. In some exemplary embodiments of the invention, the compositions are useful as substrates for chemically catalyzed conversion processes. In some embodiments, the sugars in the compositions result from hydrolysis of a cellulose containing substrate (e.g. with HCl).

As used in this specification and the accompanying claims the term "hydrolyzate" refers to a mixture of sugars resulting from hydrolysis of a cellulose containing substrate. The term hydrolyzate includes "refined hydrolyzates" prepared by application of an appropriate purification protocol to remove residual reagents from the hydrolysis process and/or separate lignin (if present) and/or adjust the sugar concentration to a desired level and/or adjust the sugar composition by enzymatic conversion. Exemplary purification protocols are described in co-pending International application publication WO/2012/106727 which is fully incorporated herein by reference. Alternatively or additionally, the term hydrolyzate includes fractionated hydrolyzates which are enriched for one or more specific sugars (e.g. glucose or mannose) or sugar types (e.g. pentoses or hexoses). In some exemplary embodiments of the invention, hydrolyzates are provided as aqueous solutions. According to various exemplary embodiments of the invention, the concentration of sugars in such an aqueous solution is 40%, 50%, 60%, 70% or 80% or intermediate or greater percentages. For example, in some embodiments the sugar concentration is 40 to 50%, 50 to 60%, 60 to 70%, 70 to 80% or greater than 80% In other exemplary embodiments of the invention, hydrolyzates are provided as a dry sugar mixture. Dried sugar mixtures can be prepared, for example, by spray drying and/or crystallization. In some embodiments, a dried sugar mixture is subsequently dissolved in water, or an aqueous solution, at a desired concentration.

As used in this specification and the accompanying claims the term "cellulose containing substrate" includes any plant derived material containing cellulose (e.g. wood, wood by-products, crop residues (e.g. cornstover, sugar cane bagasse, empty palm fruit bunches), perennial grasses, perennial woody crops and food/feed processing residues) as well as processed cellulose products (e.g. paper and cardboard)).

As used in this specification and the accompanying claims the term "cellulose sugars" refers to glucose in monomeric form and that portion of any dimer or higher oligomer composed of glucose.

As used in this specification and the accompanying claims the term "hemicellulose sugars" refers to xylose and/or arabinose and/or mannose in monomeric form and that portion of any dimer or higher oligomer composed of xylose and/or arabinose and/or mannose.

One aspect of some embodiments of the invention relates to sugar mixtures characterized by a low viscosity relative to previously available alternatives with a same dissolved solids concentration and 42 DE (Dextrose Equivalents) when assayed at the same temperature.

Another aspect of some embodiments of the invention relates to a sugar mixture containing a low level of inorganic material. In some exemplary embodiments of the invention, a reduction in the level of inorganic material in a sugar mixture contributes to a decrease in catalyst fouling and/or poisoning during the conversion process. In some exemplary embodiments of the invention, levels of sulfur are below 50 PPM, 40 PPM, 30 PPM, 20 PPM or 10 PPM (e.g. 10 to 50 PPM; 20 to 40 PPM; 35 to 50 PPM or 40 to 50 PPM). Alternatively or additionally, in some exemplary embodiments of the invention, levels of phosphorus are below 10 PPM, 7 PPM, 5 PPM or 1 PPM (e.g. 1 to 10 PPM; 1 to 7 PPM or 1 to 5 PPM or 5 to 10 PPM).

Another aspect of some embodiments of the invention relates to a level of furfurals present in the sugar mixture. As used in this specification and the accompanying claims the terms "furfurals" and "total furfurals" include both furfural and hydroxymethylfurfural. In those cases where "furfural" or "hydroxymethylfurfural" amounts or concentrations are indicated, reference is to the specific compound. In some exemplary embodiments of the invention, furfural is present due to hydrolysis of pentose-comprising polysaccharides. According to various exemplary embodiments of the invention 1, 2, 3, 4, 5, 6, 7, 8, 9 or 10 percent (or intermediate percentages) of pentoses (e.g. from hemicellulose) are degraded during the hydrolysis reaction and the resultant furfural appears in the hydrolyzate. Alternatively or additionally, in some exemplary embodiments of the invention, hydroxymethylfurfural is present due to hydrolysis of hexose-comprising polysaccharides (e.g. cellulose and/or hemicellulose). According to various exemplary embodiments of the invention According to various exemplary embodiments of the invention 1, 2, 3, 4, 5, 6, 7, 8, 9 or 10 (or intermediate percentages) of hexoses are degraded during the hydrolysis reaction and the resultant hydroxymethylfurfural appears in the hydrolyzate.

One aspect of some embodiments of the invention relates to hydrolyzates with a saccharide composition that is different than the theoretically expected saccharide yield from hydrolysis of the cellulose containing substrate. For example, if the substrate is wood, the hydrolyzate may have less glucose that expected and/or more pentoses than expected. In some exemplary embodiments of the invention, the hydrolyzate results from complete hydrolysis of hemicellulose but incomplete hydrolysis of cellulose. In some embodiments, hemicellulose and cellulose are hydrolyzed separately and the resultant hemicellulose hydrolyzate and cellulose hydrolyzate are mixed in a desired ratio to produce a hydrolyzate according to an exemplary embodiment of the invention. In some embodiments, the hydrolyzate composition is affected by sugars degradation rate during the hydrolysis. Some of the sugars in the cellulose containing substrate (e.g. lignocellulose) substrate degrade at a higher rate compared with other sugars. In some embodiments, pentoses degrade more rapidly than hexoses.

An additional aspect of some embodiments of the invention relates to sucrose present with the cellulose containing substrate prior to hydrolysis. In some exemplary embodiments of the invention, this results from incomplete processing of a sucrose crop as described in co-pending application publication WO2012/001688; which is fully incorporated herein by reference. In some exemplary embodiments of the invention, this sucrose contributes to an increase in fructose in the hydrolyzate. Alternatively or additionally, in some embodiments an enzymatic treatment is employed to increase sucrose levels. Exemplary enzymatic treatments are described hereinbelow.

Another aspect of some embodiments of the invention relates to assaying one or more specific parameters of a hydrolyzate produced in an industrial facility and using results of the assay to select a subset of hydrolyzate batches for chemical conversion. In some embodiments, batches which are not well suited to biological conversion (e.g. fermentation) are advantageously employed in chemical conversion. According to various exemplary embodiments of the invention, the one or more specific parameters assayed include viscosity and/or ash content and/or level(s) of one or more degradation product(s) and/or levels of one or more hemicellulose sugars. Degradation products include, but are not limited to, furfural and hydroxymethylfurfural.

It will be appreciated that the various aspects described above relate to solution of technical problems associated with conversion of carbohydrates in a chemically catalyzed reaction.

Alternatively or additionally, it will be appreciated that the various aspects described above relate to solution of technical problems related to fouling and/or poisoning of catalysts in a chemically catalyzed reaction.

In some exemplary embodiments of the invention, there is provided a sugar composition including: at least 40%, at least 50%, at least 60% or at least 70% dissolved solids in an aqueous solution having a viscosity at least 10% lower than a 42 DE (Dextrose Equivalents) reference solution with a same dissolved solids concentration at a given temperature (e.g. a 42% high fructose 80% solids corn syrup reference solution has a viscosity of 2200 cP at 80° F.).

In some embodiments, the dissolved solids include at least 20%, at least 30%, at least 40% or at least 50% hemicellulose sugars. Alternatively or additionally, in some embodiments, mannose comprises at least 10%, at least 15%, at least 20%, at least 25% or at least 30% of the dissolved solids and/or xylose comprises at least 5%, at least 7.5%, at least 10%, at least 12.5% or at least 15% of the dissolved solids. Alternatively or additionally, in some embodiments glucose comprises not more than 60% or not more than 55% of the dissolved solids. Alternatively or additionally, in some embodiments at least 90% of the dissolved solids are monomeric sugars. Alternatively or additionally, in some embodiments the composition includes at least 5, at least 10 or at least 15% of organic compounds including one or more compounds selected from the group consisting of alcohols, ketones, aldehydes and organic acids including 2-5 carbon atoms.

In some exemplary embodiments of the invention, there is provided a sugar composition including: at least 30%, at least 40%, at least 50% or at least 60% glucose relative to total sugars; at least 10%, at least 15%, at least 20%, at least 25% or at least 30% mannose relative to total sugars; at least 5%, at least 7.5%, at least 10%, at least 12.5% or at least 15% xylose relative to total sugars; and less than 0.25, less than 0.20, less than 0.15, less than 0.10, less than 0.05, less than 0.01 or less than 0.005% ash. In some embodiments, the composition includes less than 50, less than 30, less than 10, less than 5 or less than 1 PPM sulfur. Alternatively or additionally, in some embodiments the composition includes less than 10, less than 5, less than 3 less than 1 or less than 0.1 PPM phosphorus. Alternatively or additionally, in some embodiments the composition is provided as a solution including at least 40%, at least 50%, at least 60% or at least 70% dissolved solids. Alternatively or additionally, in some embodiments the composition includes at least 5, at least 10 or at least 15% of organic compounds including one or more compounds selected from the group consisting of alcohols, ketones, aldehydes and organic acids including 2-5 carbon atoms.

In some exemplary embodiments of the invention, there is provided a sugar composition including: at least 30%, at least 40%, at least 50% or at least 60% glucose relative to total sugars; at least 10%, at least 15%, at least 20%, at least 25% or at least 30% mannose relative to total sugars; at least 5%, at least 7.5%, at least 10%, at least 12.5% or at least 15% xylose relative to total sugars; and at least 2%, at least 3%, at least 4% or at least 5% total furfurals. In some embodiments, the composition includes not more than 15, not more than 12, or not more than 10% total furfurals. Alternatively or additionally, in some embodiments a molar ratio of furfural to pentoses is at least 0.03, at least 0.05, at least 0.07 or at least 0.09. Alternatively or additionally, in some embodiments a molar ratio of furfural to pentoses is less than 0.12 or less than 0.1. Alternatively or additionally, in some embodiments a molar ratio of hydroxymethylfurfural to hexoses is at least 0.03, at least 0.05, at least 0.07 or at least 0.09. Alternatively or additionally, in some embodiments a molar ratio of hydroxymethylfurfural to hexoses is less than 0.12 or less than 0.1. Alternatively or additionally, in some embodiments a molar ratio of carboxylic acids (e.g. acetic and/or formic and/or galactauronic and/or levulinic acids) to sugars is at least 0.03, at least 0.05, at least 0.07 or at least 0.09. Alternatively or additionally, in some embodiments a molar ratio of carboxylic acids to sugars is less than 0.12 or less than 0.1.

In some exemplary embodiments of the invention, there is provided a sugar composition, including: at least 30, at least 40, at least 50, at least 60 or at least 70% hemicellulose sugars relative to total sugars; and 20 to 60% cellulose sugars relative to total sugars. In some embodiments, the composition includes at least 10%, at least 15%, at least 20%, at least 25% or at least 30% mannose relative to total sugars. Alternatively or additionally, in some embodiments the composition includes at least 5%, at least 7.5%, at least 10%, at least 12.5% or at least 15% xylose relative to total sugars. Alternatively or additionally, in some embodiments the composition includes at least 5%, at least 7.5%, at least 10%, at least 12.5% or at least 15% fructose relative to total sugars.

In some exemplary embodiments of the invention, there is provided a sugar composition including at least 10% fructose relative to total sugars; and at least 10% hemicellulose sugars relative to total sugars. In some embodiments, the composition includes at least 15% or at least 20% fructose. Alternatively or additionally, in some embodiments the composition includes at least 15% or at least 20% hemicellulose sugars. Alternatively or additionally, in some embodiments the composition is provided as an aqueous solution including at least 60% dissolved solids. Alternatively or additionally, in some embodiments the composition includes at least 5, at least 10 or at least 15% of organic compounds including one or more compounds selected from the group consisting of alcohols, ketones, aldehydes and organic acids including 2-5 carbon atoms.

In some exemplary embodiments of the invention, there is provided a sugar composition comprising (relative to dry solids): (a) at least 49% glucose; (b) at least 9.5% xylose; (c) at least 2.5% arabinose; and (d) at least 25% mannose.

In some exemplary embodiments of the invention, there is provided a method including: producing a sugar composition as described hereinabove; and converting sugars in the sugar composition to a conversion product in a chemically catalyzed reaction. In some embodiments, the producing includes hydrolyzing a substrate including cellulose to produce a hydrolyzate. In some embodiments, the hydrolyzing includes refining the hydrolyzate.

In some exemplary embodiments of the invention, there is provided a method including
hydrolyzing not more than 90% of cellulose in a cellulose including substrate to produce a hydrolyzate; and
converting sugars in the hydrolyzate to a conversion product in a chemically catalyzed reaction.

In some exemplary embodiments of the invention, there is provided a method including: providing a conversion product as described hereinabove; and processing the conversion product to produce a processed product.

According to various exemplary embodiments of the invention, the processed product includes one or more members selected from the group consisting of terephthalic acid, polymers of terephthalic acid, a fuel ingredient, a paraffin a polyethylene, a polystyrene, a polypropylene, butyl acrylate, butyl acetate, dibutyl phthalate, dibutyl sebacate, other butyl esters, ethylene glycol, monobutyl ether, di-ethylene glycol, triethylene glycol, monobutyl ether, isobutyl acetate and butanone (MEK).

In some exemplary embodiments of the invention, there is provided a processed product produced by a method as described hereinabove.

In some exemplary embodiments of the invention, there is provided a method including
providing a processed product as described hereinabove; and
subjecting the processed product to an industrial process to produce a downstream product.

According to various exemplary embodiments of the invention, the downstream product is selected from the group consisting of a liquid fuel and a polymeric plastic.

In some exemplary embodiments of the invention, there is provided a downstream product produced by a method as described hereinabove.

In some exemplary embodiments of the invention, there is provided a method including
providing a processed product as described hereinabove; and
using the processed product as an ingredient or component in a downstream product.

According to various exemplary embodiments of the invention, the downstream product is selected from the group consisting of a liquid fuel, a super absorbent gel, a paint, a dye, a glue, a fabric and a plastic item.

In some exemplary embodiments of the invention, there is provided a downstream product produced by a method as described hereinabove.

REPRESENTATIVE EMBODIMENTS

The following embodiments of the disclosure are provided by way of example only:

1. A sugar composition comprising:
   at least 40% dissolved solids in an aqueous solution having a viscosity at least 10% lower than a 42 DE (Dextrose Equivalents) reference solution with a same dissolved solids concentration at a given temperature.
2. A composition according to embodiment 1, wherein the dissolved solids comprise at least 20% hemicellulose sugars.
3. A composition according to embodiment 1 or embodiment 2, wherein mannose comprises at least 10% of the dissolved solids and/or xylose comprises at least 5% of the dissolved solids.
4. A composition according to any of embodiments 1 to 3, wherein glucose comprises less than 60% of the dissolved solids.
5. A composition according to any of embodiments 1 to 4, wherein at least 90% of the dissolved solids are monomeric sugars.
6. A composition according to any of embodiments 1 to 5, comprising at least 5% of organic compounds comprising one or more compounds selected from the group consisting of alcohols, ketones, aldehydes and organic acids comprising 2-5 carbon atoms.
7. A sugar composition comprising:
   at least 30% glucose relative to total sugars;
   at least 10% mannose relative to total sugars;
   at least 5% xylose relative to total sugars; and
   less than 0.25% ash.
8. A composition according to embodiment 7, comprising less than 50 PPM sulfur.
9. A composition according to embodiment 7 or 8, comprising less than 10 PPM phosphorus.
10. A composition according to any of embodiments 7 to 9, provided as a solution comprising at least 40% dissolved solids.
11. A composition according to any of embodiments 7 to 10, further comprising at least 5% of organic compounds comprising one or more compounds selected from the group consisting of alcohols, ketones, aldehydes and organic acids comprising 2-5 carbon atoms.
12. A sugar composition comprising:
   at least 30% glucose relative to total sugars;
   at least 10% mannose relative to total sugars;
   at least 5% xylose relative to total sugars; and
   at least 2% total furfurals.
13. A composition according to embodiment 12, comprising not more than 15% total furfurals.

14. A composition according to embodiment 12 or 13, wherein a molar ratio of furfural to pentoses is at least 0.03.
15. A composition according to any of embodiments 12 to 14, wherein a molar ratio of furfural to pentoses is less than 0.12.
16. A composition according to any of embodiments 12 to 15, wherein a molar ratio of hydroxymethylfurfural to hexoses is at least 0.03.
17. A composition according to any of embodiments 12 to 16, wherein a molar ratio of hydroxymethylfurfural to hexoses is less than 0.12.
18. A composition according to any of embodiments 12 to 17, wherein a molar ratio of carboxylic acids to sugars is at least 0.03.
19. A composition according to any of embodiments 12 to 18, wherein a molar ratio of carboxylic acids to sugars is less than 0.12.
20. A sugar composition, comprising:
   at least 30% hemicellulose sugars relative to total sugars; and
   20% to 60% cellulose sugars relative to total sugars.
21. A composition according to embodiment 20, comprising at least 10% mannose relative to total sugars.
22. A composition according to embodiment 20 or 21, comprising at least 5% xylose relative to total sugars.
23. A composition according to any of embodiments 20 to 22, comprising at least 5% fructose relative to total sugars.
24. A sugar composition comprising:
   at least 10% fructose; and
   at least 10% hemicellulose sugars.
25. A composition according to embodiment 24, comprising at least 15% fructose.
26. A composition according to embodiment 24 or 25, comprising at least 15%, hemicellulose sugars.
27. A composition according to any of embodiments 24 to 26, provided as an aqueous solution comprising at least 60% dissolved solids.
28. A composition according to any of embodiments 24 to 27, further comprising at least 5% of organic compounds comprising one or more compounds selected from the group consisting of alcohols, ketones, aldehydes and organic acids comprising 2-5 carbon atoms.
29. A sugar composition comprising (relative to dry solids):
   (a) at least 49% glucose;
   (b) at least 9.5% xylose;
   (c) at least 2.5% arabinose; and
   (d) at least 25% mannose.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

As used herein, the terms "comprising" and "including" or grammatical variants thereof are to be taken as specifying inclusion of the stated features, integers, actions or components without precluding the addition of one or more additional features, integers, actions, components or groups thereof.

The phrase "adapted to" as used in this specification and the accompanying claims imposes additional structural limitations on a previously recited component.

Percentages (%) of insoluble carbohydrates (e.g. cellulose), sugars, saccharides, furfurals and ash (total and individual components) are W/W (weight per weight) relative to total solids unless otherwise indicated. Concentrations indicated in PPM are also on a total solids basis unless otherwise indicated. As used in this specification and the accompanying claims the term "total solids" indicates dry matter which remains after all water is evaporated.

BRIEF DESCRIPTION OF THE DRAWINGS

In order to understand the invention and to see how it may be carried out in practice, embodiments will now be described, by way of non-limiting example only, with reference to the accompanying figures. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are:

FIG. 2 is a simplified flow diagram of a method according to some exemplary embodiments of the invention.

DETAILED DESCRIPTION OF EMBODIMENTS

Figure 1:
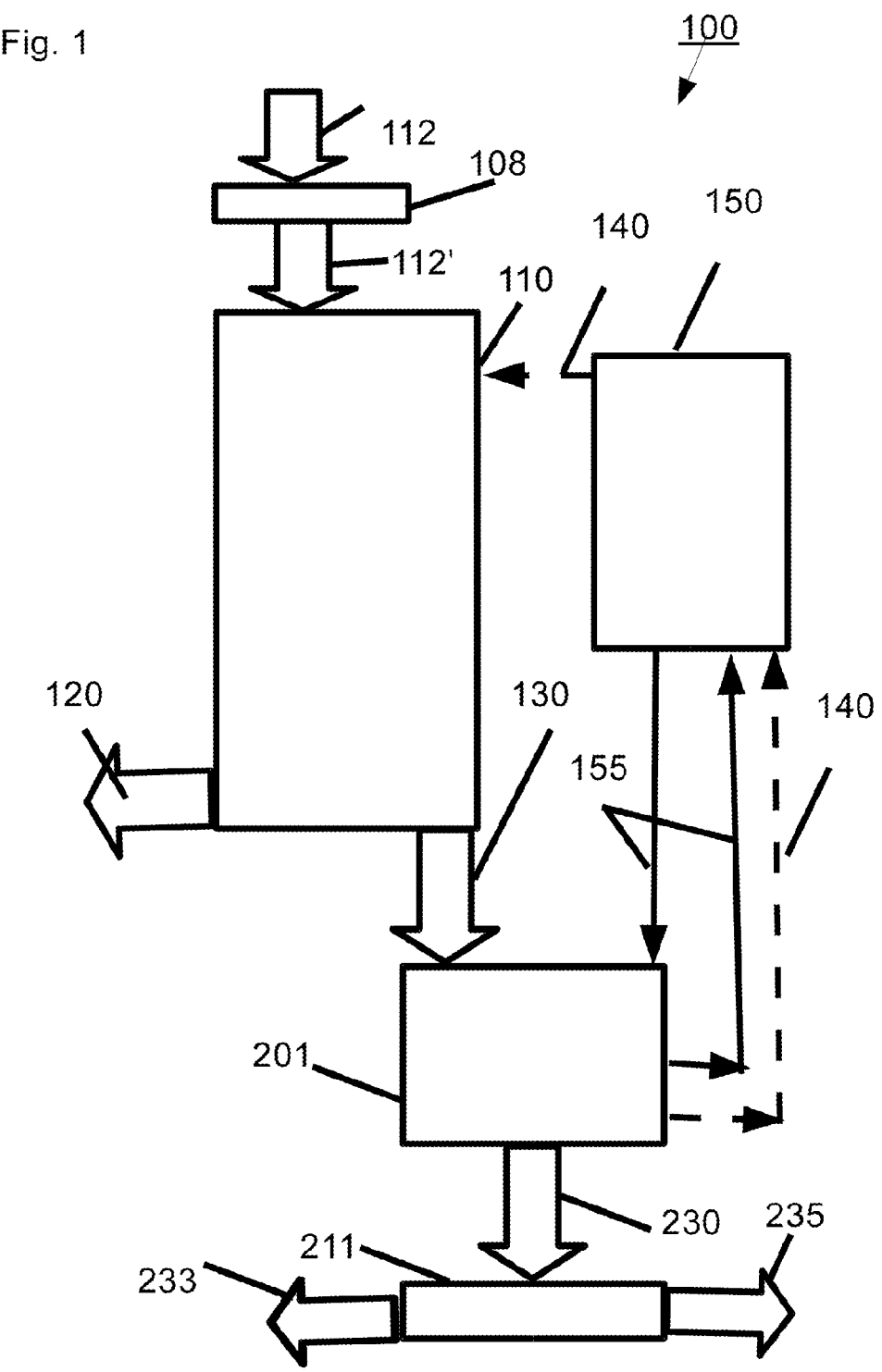
FIG. 1 is schematic overview of a system according some exemplary embodiments of the invention.

Embodiments of the invention relate to sugar compositions. According to various exemplary embodiments of the invention the sugar compositions are provided in liquid or solid form.

Specifically, sugar compositions according to various embodiments of the invention can serve as input streams for chemical conversion to a conversion product. Some exemplary embodiments of the invention relate to conversion products produced by such a chemical conversion. Exemplary conversion products include, but are not limited to hydrocarbons (e.g. para-xylene), oxygenated hydrocarbons, non-condensable gas products, alcohols and hydrogen gas. In some exemplary embodiments of the invention, these conversion products are characterized by an O/C ratio less than 1.5; less than 1.0; less than 0.75; less than 0.5; less than 0.3; less than 0.2 or less than 0.1.

Compositions according to exemplary embodiments of the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is illustrative and not limiting.

Exemplary System Overview

FIG. 1 is a simplified schematic diagram of a system for acid hydrolysis of a substrate including cellulose indicated generally as 100. Depicted system 100 includes a main hydrolysis reactor 110 adapted to receive an input substrate 112. In many cases substrate 112 is provided as wood chips, although any cellulose containing substrate can be used instead of wood. In some exemplary embodiments of the invention, substrate 112 is subjected to a pretreatment in pretreatment module 108 to produce a modified substrate 112'. In some embodiments, a pretreatment conducted in module 108 produces one or more streams containing ash and/or sugars (additional streams not depicted). Exemplary pretreatments are described in international application publication WO/2012/079021; which is fully incorporated herein by reference.

Additional exemplary substrates 112 include, but are not limited to, sugar cane bagasse, sugar beets and/or their cossettes, corn stover, post harvest plants (e.g. cotton, soybean or rapeseed), switchgrass, broomgrass, paper and cardboard.

In the depicted exemplary system, substrate 112 is brought into contact with a concentrated HCl solution in reactor 110 and hemicellulose and/or cellulose in the substrate are hydrolyzed to produce a mixture of soluble sugars and, optionally, residual lignin. These materials are collected separately as lignin stream 120 (if present) and crude hydrolyzate 130, each of which contains a high concentrations of HCl.

Details of exemplary hydrolysis methods and systems are described in co-pending International application publication WO2012/061085; which is fully incorporated herein by reference. According to various exemplary embodiments of the invention the way in which hydrolysis is conducted in reactor 110 contributes to the composition of crude hydrolyzate 130 and/or lignin stream 120. Affecting parameters include, but are not limited to, initial substrate moisture, reactor design, mode of hydrolysis (e.g. co-current contact, counter-current contact and combinations thereof), number of hydrolysis stages and acid concentration and/or temperature and/or residence time in each hydrolysis stage. The composition of crude hydrolyzate 130 and/or lignin stream 120 is influenced by the amount of sugar degradation products produced at 110 and/or 201 and/or by the yield of specific intact sugars produced at 110 and/or remaining after 201 (e.g. pentoses such as xylose and/or hexoses such as glucose).

Crude hydrolyzate 130 is processed to remove HCl and/or adjust the mixture to achieve one or more desired ratios of mixture components (e.g. disaccharides and/or monosaccharides). Parameters of HCl removal also affect the composition of the deacidified hydrolyzate, including the mode of removal, e.g. distillation vs. solvent extraction, solvent choice, e.g. its selectivity and water co-extraction, contactors design, number of theoretical stages in the solvent extraction, temperature of each stage and residence time in each stage. This processing is conducted in a hydrolyzate refining module, designated here generically as 201.

In some embodiments, additional hydrolyzate (similar to 130) is recovered from lignin stream 120 as described in co-pending International application publication WO/2011/151823 which is fully incorporated herein by reference. In some exemplary embodiments of the invention, this additional hydrolyzate is routed (not depicted) to refining module 201. According to various exemplary embodiments of the invention this additional hydrolyzate increases a total sugar yield and/or changes a composition of mixture (e.g. refined hydrolyzate 230).

In depicted system 100, hydrolyzate refining module 201 employs a flow of organic solvent 155 (solid arrows) to extract HCl 140 (dashed arrows) from crude hydrolyzate 130.

Refined hydrolyzate 230 containing a mixture of de-acidified sugars is the primary product of refining module 201. In some embodiments, sugars recovered from pretreatment module 108 and/or lignin stream 120 are also present in refined hydrolyzate 230. Module 201 also produces a stream of HCl 140 mixed with solvent 155 (depicted as parallel dashed and solid arrows respectively for clarity) which is routed to a solvent/HCl recovery module 150. Recovery module 150 separates HCl 140 from solvent 155. In some exemplary embodiments of the invention, separation is by distillation. HCl 140 is recycled to hydrolysis reactor 110 and solvent 155 is recycled to refining module 201. Details of HCl and solvent recycling are described in co-pending international application publication WO/2012/081740 and US application publication 2012/0167874; each of which is fully incorporated by reference.

Refined hydrolyzate 230 includes a mixture of de-acidified sugars. Various components of the mixture can be chemically converted to conversion products. In some cases, implementation of specific chemical conversion processes is influenced by an initial composition of refined hydrolyzate 230. In many cases, refined hydrolyzate 230 contains glucose as a primary component since glucose is a primary component of cellulose in substrate 112. Alternatively or additionally, in many cases, sugar mixture 230 contains a significant amount of xylose since xylose is often the most prevalent saccharide component of hemicellulose in substrate 112.

In some exemplary embodiments of the invention, refined hydrolyzate 230 is assayed with respect to one or more parameters in an assay module 211. Depending upon the results of the assay(s), refined hydrolyzate 230 is routed to chemical conversion 233 or biological conversion 235 (e.g. fermentation).

Exemplary Chemical Conversion Processes

Exemplary chemically catalyzed processes for conversion of biomass derived sugars to conventional liquid fuels through a multistep catalytic conversion process are disclosed in U.S. Pat. No. 7,038,094; U.S. Pat. No. 6,486,366; U.S. Pat. No. 6,479,713; U.S. Pat. No. 8,277,643; U.S. Pat. No. 7,880,049; U.S. Pat. No. 4,503,278; U.S. Pat. No. 8,017,818; U.S. Pat. No. 7,977,517; U.S. Pat. No. 7,038,094; U.S. Pat. No. 6,841,085; U.S. Pat. No. 6,124,443; U.S. Pat. No. 8,084,508; U.S. Pat. No. 6,136,868; U.S. Pat. No. 5,856,261; U.S. Pat. No. 8,277,643; U.S. Pat. No. 7,947,858; U.S. Pat. No. 7,704,381; U.S. Pat. No. 5,856,261; U.S. Pat. No. 8,152,867; U.S. Pat. No. 7,935,156; U.S. Pat. No. 7,942,940; U.S. Pat. No. 8,026,378; U.S. Pat. No. 8,053,468; U.S. Pat. No. 8,084,635; U.S. Pat. No. 8,178,701; and U.S. Pat. No. 8,188,030. The contents of each of these patents are fully incorporated herein by reference.

Exemplary Compositions

Some exemplary embodiments of the invention, relate to sugar compositions suitable for use as inputs in a catalytic conversion processes.

In some exemplary embodiments of the invention, the sugar composition includes at least 40%, at least 50%, at least 60% or at least 70% dissolved solids in an aqueous solution having a viscosity which is at least 10%, 20%, 30%, 40% or 50% lower than a 42 DE (Dextrose Equivalents) solution with a same dissolved solids concentration at a given temperature. Viscosity influences flow properties which may be relevant to conversion processes 233 and/or 235. According to various exemplary embodiments of the invention the dissolved solids comprise at least 20%, at least 30%, at least 40% or at least 50% hemicellulose sugars.

In some exemplary embodiments of the invention, at least 10%, 15%, 20%, 25% or 30% (or intermediate or greater percentages) of the dissolved solids are mannose. Alternatively or additionally, at least 5%, 7.5%, 10%, 12.5% or 15% (or intermediate or greater percentages) of the dissolved solids are xylose. According to various exemplary embodiments of the invention mannose and xylose are present as monomeric sugars and/or as portions of oligomeric sugars (dimers or higher).

In some exemplary embodiments of the invention, less than 60%, or less than 55%, of the dissolved solids is glucose.

Alternatively or additionally, the dissolved solids in the composition include at least 90%, at least 92% or at least 94% monomeric sugars.

Alternatively or additionally, in some embodiments the composition includes at least 5%, 6%, 7%, 8%, 9% or 10% of organic compounds such as alcohols and/or ketones and/or aldehydes and/or organic acids comprising 2-5 carbon atoms.

Some exemplary embodiments of the invention relate to a composition including at least 30%, 40%, 50% or 60% (or intermediate or greater percentages) glucose relative to total sugars, at least 10%, at least 15%, at least 20%, at least 25%, at least 30% (or intermediate or greater percentages) mannose relative to total sugars and at least 5%, at least 7.5%, at least 10%, at least 12.5% or at least 15% (or intermediate or greater percentages) xylose relative to total sugars and less than 0.25% or less than 0.15% ash. In some embodiments, compositions of this type include less than 50, less than 10, less than 5 or less than 2 PPM sulfur (or intermediate or lower amounts). Alternatively or additionally, compositions of this type include less than 10, less than 7, less than 5, less than 2 or less than 1 PPM phosphorus (or intermediate or lower amounts). Alternatively or additionally, in some embodiments compositions of this type are provided as an aqueous solution with at least 40%, at least 50%, at least 60%, at least 70% dissolved solids (or intermediate or higher percentages).

Alternatively or additionally, in some embodiments the composition includes at least 5%, 6%, 7%, 8%, 9% or 10% of organic compounds such as alcohols and/or ketones and/or aldehydes and/or organic acids comprising 2-5 carbon atoms.

Some exemplary embodiments of the invention relate to a sugar composition including at least 30%, at least 40%, at least 50% or at least 60% glucose (or intermediate or higher percentages) relative to total sugars and at least 2%, at least 3%, at least 4%, at least 5% total furfurals (or intermediate or higher percentages).

In some embodiments of the invention, the composition includes at least 10%, at least 15%, at least 20%, at least 25% or at least 30% mannose (or intermediate or higher percentages) relative to total sugars. Alternatively or additionally, in some exemplary embodiments of the invention the composition includes at least 5%, at least 7.5%, at least 10%, at least 12.5% or at least 15% xylose (or intermediate or higher percentages) relative to total sugars.

In some embodiments, the composition includes not more than 15 or not more than 10% total furfurals. In some exemplary embodiments of the invention, a molar ratio of furfural to pentoses is at least 0.03, 0.05, 0.06, 0.065, 0.07 or at least 0.075. Alternatively or additionally, the molar ratio of furfural to pentoses is less than 0.12, 0.115, 0.11, 0.105 or less than 0.1. Alternatively or additionally, a molar ratio of hydroxymethylfurfural to hexoses is at least 0.03, 0.05, 0.06, 0.065, 0.07 or at least 0.075. Alternatively or additionally, a molar ratio of hydroxymethylfurfural to hexoses is less than 0.12 or less than 0.1. In some embodiments, compositions of this type are provided as an aqueous solution with at least 40%, at least 50%, at least 60% or at least 70% dissolved solids (or intermediate or higher percentages).

In some embodiments, a molar ratio of carboxylic acids to sugars in the composition is at least 0.03. Alternatively or additionally, in some embodiments a molar ratio of carboxylic acids to sugars in the composition is less than 0.12.

Some exemplary embodiments of the invention relate to a sugar composition including at least 30%, at least 40%, at least 45% or at least 50% (or intermediate or higher percentages) hemicellulose sugars (relative to total sugars) and 20%, 30%, 40%, 50%, 55% or 60% (or intermediate or higher percentages) glucose (relative to total sugars). Alternatively or additionally, in some embodiments a composition of this type includes at least 10%, at least 15%, at least 20%, at least 25% or at least 30% (or intermediate or higher percentages) mannose (relative to total sugars) and/or at least 5%, at least 7.5%, at least 10%, at least 12.5% or at least 15% (or intermediate or higher percentages) xylose (relative to total sugars). Alternatively or additionally, a composition of this type includes 5%, at least 7.5%, at least 10%, at least 12.5% or at least 15% (or intermediate or higher percentages) fructose (relative to total sugars). In some embodiments, fructose results from use of a hydrolysis substrate 112 (FIG. 1) including sucrose as described in International application publication WO2012/001688 which is fully incorporated herein by reference.

Alternatively or additionally, use of a hydrolysis substrate 112 including sucrose produces a sugar composition including at least 10%, at least 15% or at least 20% fructose (or intermediate or higher percentages); and at least 10%, at least 15% or at least 20% sugars derived from hemicellulose (or intermediate or higher percentages). According to various exemplary embodiments of the invention the sugars derived from hemicellulose include xylose and/or mannose and/or arabinose. In some exemplary embodiments of the invention, compositions of this type are provided as an aqueous solution including at least 60%, 65%, 70% or 75% dissolved solids. Alternatively or additionally, in some embodiments compositions of this type are provided as an aqueous solution with at least 40%, at least 50%, at least 60%, at least 70% dissolved solids (or intermediate or higher percentages).

Alternatively or additionally, crude hydrolyzate 130 and/or refined hydrolyzate 230 are enzymatically treated to convert at least a portion of the glucose therein to fructose. For example, a xylose isomerase (Enzyme commission number EC 5.3.1.5; also known as glucose isomerase) can be used to convert glucose to fructose as is done in the high fructose corn syrup industry.

Some exemplary embodiments of the invention, relate to a sugar composition comprising (relative to dry solids) at least 49% glucose; at least 9.5% xylose; at least 2.5% arabinose; and at least 25% mannose.

Exemplary Viscosity Assay Protocol

In some embodiments of the invention, a comparison is made between a sample (e.g. refined hydrolyzate 230) and a reference solution. In order to make this comparison, a measurement of percentage of total dissolved solids in the sample (e.g. hydrolyzate 230) is made (e.g. by evaporation to dryness). If the reference solution is not labeled as to total dissolved solids concentration, a measurement of the dissolved solids concentration in the reference solution is conducted using the same measurement technique as for the sample. Once the total dissolved solids concentration of the sample and the reference solution are known, the reference solution is adjusted to the same dissolved solids concentration as the sample by dilution, or evaporation, as needed. In some exemplary embodiments of the invention, a 42 Dextrose Equivalents (DE) solution serves as a reference solution. One example of a suitable reference solution is Iso-Clear® 42% high fructose 80% solids corn syrup (Cargill; Regional Sweeteners Office; Lancaster Pa.; USA).

In some embodiments, a reference solution with a concentration of dissolved solids higher than the composition being assayed is selected. Use of a reference solution with a higher concentration of dissolved solids allows adjustment of the reference solution by dilution.

Once the reference solution and the composition being assayed are at the same dissolved solids concentration, the viscosity of each is measured at a given temperature (e.g. 25; 30; 35; 40; 45; 50; 55 or 60° C.). A sugar composition (e.g. refined hydrolyzate 230) with a viscosity at least 10% lower than a 42 DE reference solution with the same dissolved solids concentration (measured under the same conditions) is an exemplary embodiment of the invention.

Exemplary Parameter Assay Considerations

Referring again to FIG. 1, in some embodiments refined hydrolyzate 230 is assayed with respect to one or more specific parameters. According to various exemplary embodiments of the invention the specific parameters include viscosity and/or ash content and/or degradation product level and/or levels of one or more hemicellulose sugars.

With regard to viscosity, an increase in viscosity can contribute to problems (e.g. decreased reaction rate and/or decreased yield) in chemically catalyzed conversion processes 233, particularly using heterogeneous catalyst, where reaction rate AO reaction kinetics are diffusion controlled. Traditionally, implementation of a temperature increase during the chemically catalyzed conversion was undertaken in an attempt to mitigate these problems as viscosity typically decreases with temperature elevation. However, increase of temperature beyond a certain point can contribute to undesired degradation of sugars. Elevated temperature reactions are more difficult to control and therefore lead to side degradation reactions resulting in undesired products, e.g. large condensation products and coking. Some exemplary embodiments of the invention are compositions with at least 40% dissolved solids in an aqueous solution having a viscosity at least 10% lower than a 42 DE (Dextrose Equivalents) reference solution with a same dissolved solids concentration at a given temperature.

In some embodiments, a viscosity assay of refined hydrolyzate 230 is used to identify a sugar composition including at least 40%, at least 50%, at least 60% or at least 70% dissolved solids having a viscosity at least 10% lower than a 42 DE (Dextrose Equivalents) solution of similar concentration at a given temperature. In some embodiments, the dissolved solids include at least 20%, at least 30%, at least 40% or at least 50% hemicellulose sugars (or intermediate or higher percentages). In some embodiments, refined hydrolyzate 230 includes at least 10%, 15%, 20%, 25% or 30% or more mannose as a percentage of the dissolved solids. Alternatively or additionally, in some embodiments refined hydrolyzate 230 includes at least 5%, 7.5%, 10%, 12.5%, or 15% or more xylose as a percentage of the dissolved solids. In some embodiments, a refined hydrolyzate 230 with a viscosity at or below a pre-determined threshold level is selected for routing to a chemical conversion process 233. Alternatively or additionally, in some embodiments a refined hydrolyzate 230 with a viscosity above a pre-determined threshold level is mixed with a second sugar stream to decrease viscosity and produce a mixed stream suitable for routing to a chemical conversion process 233. In some embodiments, the second sugar stream includes more non-glucose sugars than refined hydrolyzate 230.

In some embodiments, an assay of organic compounds (e.g. by HPLC or gas chromatography) in refined hydrolyzate 230 is used to identify a sugar composition including at least 5, at least 10 or at least 15% organic compounds (e.g. alcohols, ketones, aldehydes and organic acids including 2-5 carbon atoms). While these organic compounds may have an inhibitory effect on biological processes, they can be introduced into a chemical conversion process 233 with little or no effect (Z. R. Ismagilov et al. (2008) Energy Environ. Sci. 1:526-541 and A. Holmen (2009) Catalysis Today 142:2-8). In some embodiments, the organic compounds serve as a substrate for the chemical conversion process 233 and are converted to additional conversion product(s). Thus, in some embodiments a refined hydrolyzate 230 with an organic compounds content at or above a pre-determined threshold level is selected for routing to a chemical conversion process 233. In some embodiments, assay of organic compound levels is conducted in conjunction with assay of viscosity.

In some embodiments, an assay of ash (e.g. by complete combustion) in refined hydrolyzate 230 is used to identify a sugar composition including less than 0.25, less than 0.20, less than 0.15, less than 0.10, less than 0.05, less than 0.01 or less than 0.005% ash. In contrast to organic compounds, increasing the level of ash would not be expected to have a significant negative impact on biological conversion 235, but is expected to contribute to increased catalyst fouling and/or catalyst poisoning in a chemical conversion process 233. In some exemplary embodiments of the invention, assays of specific ash components are conducted. For example, in some embodiments the assay identifies refined hydrolyzates 230 including less than 50, less than 30, less than 10, less than 5 or less than 1 PPM sulfur. Alternatively or additionally, in some embodiments the assay identifies refined hydrolyzates 230 including less than 10, less than 5, less than 3, less than 1 or less than 0.1 PPM phosphorus. According to various exemplary embodiments of the invention assays of ash, or specific components of ash (e.g. sulfur and/or phosphorus), are conducted in conjunction with assays of viscosity and/or with assays of organic compound levels. Multiple assays can be conducted in conjunction with one another by taking multiple samples and sending each sample to a specific assay in parallel.

In some embodiments, an assay of degradation products (e.g. furfurals) in refined hydrolyzate 230 is used to identify a sugar composition having a relatively high level of degradation products. Assays for measurement of furfurals include, but are not limited to, gas chromatography and colorimetric assays.

Furfurals have a negative impact on many biological conversion processes but can serve as a substrate for many chemical conversion processes. In some embodiments the assay of degradation products identifies refined hydrolyzates 230 with at least 2%, at least 3%, at least 4% or at least 5% total furfurals and/or sugar compositions with not more than 15%, not more than 12% or not more than 10% total furfurals.

In some exemplary embodiments of the invention, pentoses and/or hexoses are measured in parallel to furfurals so that molar ratio scan be calculated.

In some embodiments, the assay identifies refined hydrolyzates with a molar ratio of furfural to pentoses of at least 0.03, at least 0.05, at least 0.07 or at least 0.09 and/or refined hydrolyzates 230 with a molar ratio of furfural to pentoses less than 0.12 or less than 0.1. Alternatively or additionally, in some embodiments the assay identifies refined hydrolyzates 230 with a molar ratio of hydroxymethylfurfural to hexoses of at least 0.03, at least 0.05, at least 0.07 or at least 0.09 and/or a molar ratio of hydroxymethylfurfural to hexoses less than 0.12 or less than 0.1. In some embodiments, the assay of degradation products is conducted in parallel with an assay of carboxylic acids and identifies refined hydrolyzates 230 with a molar ratio of carboxylic acids to sugars of at least 0.03, at least 0.05, at least 0.07 or at least 0.09 and/or with a molar ratio of carboxylic acids to sugars less than 0.12 or less than 0.1. According to various exemplary embodiments of the invention assays of degradation product level are conducted in parallel with assays of ash (or specific components of ash) and/or with assays of viscosity and/or with assays of organic compound levels.

In some embodiments, an assay of hemicellulose sugars in refined hydrolyzate 230 is used to identify a sugar composition having a relatively high level of hemicellulose sugars. These hemicellulose sugars originate from module 108 and/or from reactor 110. Hemicellulose sugars are not well utilized by many biological conversion processes 235 but can serve as a substrate for many chemical conversion processes 233, e.g. xylose hydrogenation to xylitol or hemicellulose sugars dehydration to furfural and furfural conversion to levulinic acid.

In some embodiments the assay of hemicellulose sugars identifies refined hydrolyzates 230 with at least 30, at least 40, at least 50, at least 60 or at least 70% hemicellulose sugars relative to total sugars; and 20 to 60% cellulose sugars relative to total sugars. According to various exemplary embodiments of the invention the assay identifies refined hydrolyzates 230 including at least 10%, at least 15%, at least 20%, at least 25% or at least 30% mannose relative to total sugars. Alternatively or additionally, according to various exemplary embodiments of the invention the assay identifies refined hydrolyzates 230 including at least 5%, at least 7.5%, at least 10%, at least 12.5% or at least 15% xylose relative to total sugars. Alternatively or additionally, according to various exemplary embodiments of the invention the assay identifies refined hydrolyzates 230 including at least 5%, at least 7.5%, at least 10%, at least 12.5%, or at least 15% fructose relative to total sugars.

According to various exemplary embodiments of the invention assays of hemicellulose sugar levels are conducted in parallel with assays of degradation product level and/or with assays of ash (or specific components of ash) and/or with assays of viscosity and/or with assays of organic compound levels.

Exemplary Fructose Enrichment

In some embodiments refined hydrolyzate 230 is subjected to fructose enrichment (e.g. via enzymatic treatment) to produce a composition including at least 10%, 15% or 20% fructose and at least 10%, 15% or 20% hemicellulose sugars.

According to various exemplary embodiments of the invention the resultant composition includes at least 60% dissolved solids and/or at least 5%, at least 10% or at least 15% of organic compounds as described above. In some embodiments, fructose enrichment contributes to a reduction in viscosity. Alternatively or additionally, in some embodiments some chemical conversion processes 233 operate more efficiently with fructose than with glucose.

Exemplary Furfural Concentration Adjustment

As described above, furfurals (or their degradation products such as levulinic acid) can adversely affect biological conversion 235 but are acceptable in chemical conversion 233 (FIG. 1). In some embodiments, refined hydrolyzate 230 is divided into two portions, one of which is directed to chemical conversion 233 and another of is directed to biological conversion 235.

The portion of refined hydrolyzate 230 destined for biological conversion 235 is purified to remove furfurals. According to various exemplary embodiments of the invention, purification to remove furfurals includes distillation and/or chromatographic separation. This purification reduces the furfural concentration sufficiently that the purified portion of refined hydrolyzate 230 can be used in biological conversion 235.

According to these embodiments, the furfurals removed during purification are then added back to the portion of refined hydrolyzate 230 destined for chemical conversion 233. In these embodiments of the invention, a loss of sugar yield from substrate 112 as a result of degradation to furfurals during hydrolysis 110 is at least partially offset by conversion of the furfurals to useful products in chemical conversion 233.

Exemplary Further Processing

FIG. 2 is a simplified flow diagram depicting exemplary methods for further processing conversion products indicated generally as 300.

In some exemplary embodiments of the invention, method 300 includes providing 310 a conversion product (e.g. from a chemical conversion process 233 or a biological conversion process 235) and processing 320 the conversion product to produce a processed product 330.

In some exemplary embodiments of the invention, the processed product includes one or more members selected from the group consisting of terephthalic acid, polymers of terephthalic acid, a fuel ingredient, a paraffin a polyethylene, a polystyrene, a polypropylene, butyl acrylate, butyl acetate, dibutyl phthalate, dibutyl sebacate, other butyl esters, ethylene glycol, monobutyl ether, di-ethylene glycol triethylene glycol, monobutyl ether, isobutyl acetate and butanone (MEK).

In some exemplary embodiments of the invention, the conversion product includes paraxylene (p-xylene) and processed product 330 includes terephthalic acid. For example, paraxylene can be formed by dehydroaromatization (see for example Z. R. Ismagilov et al. (2008) Energy Environ. Sci. 1:526-541 and A. Holmen (2009) Catalysis Today 142:2-8).

A processed product produced by a method as described above is an additional exemplary embodiment of the invention.

Alternatively or additionally, the depicted further processing method 300 can include providing a processed product 330 and subjecting said processed product to an industrial process 340 to produce a downstream product 350 in some embodiments.

In some embodiments, downstream product 350 is a liquid fuel and/or a polymeric plastic.

A downstream product 350 produced by a method as described above is an additional exemplary embodiment of the invention.

Alternatively or additionally, the depicted further processing method 300 includes providing a processed product 330 and using 345 processed product 330 as an ingredient or component in a downstream product 350 in some embodiments.

According to various exemplary embodiments of the invention downstream product 350 is a liquid fuel and/or a super absorbent gel and/or a paint and/or a dye, and/or a glue and/or a fabric and/or a plastic item. For example, plastic items according to some exemplary embodiments of the invention may be PET and/or PETA products such as bottles or food wrappers. Alternatively or additionally, fabrics may be woven or non-woven fabrics (e.g. as commonly used in moist towelettes).

Downstream product 350 produced by a method 300 as described above are exemplary embodiments of the invention.

It is expected that during the life of this patent many non-enzymatic catalysts will be developed and the scope of the invention is intended to include all such new technologies a priori.

Although the invention has been described in conjunction with specific embodiments, many alternatives, modifications and variations will be apparent to those skilled in the art. Accordingly, the application embraces all such alternatives, modifications and variations that fall within the scope of the appended claims.

Specifically, numerical indicators used in the application could vary even further based upon engineering principles and/or materials and/or intended use and/or designs incorporated into various embodiments of the invention. Additionally, components and/or actions ascribed to exemplary embodiments of the invention and depicted as a single unit may be divided into subunits. Conversely, components and/or actions ascribed to exemplary embodiments of the invention and depicted as sub-units/individual actions may be combined into a single unit/action with the described/depicted function.

Alternatively, or additionally, features used to describe a method can be used to characterize an apparatus and features used to describe an apparatus can be used to characterize a method.

It should be further understood that the individual features described hereinabove can be combined in all possible combinations and sub-combinations to produce additional embodiments of the invention. The examples given above are purely illustrative and do not limit the scope of the invention which is defined solely by the following claims. Specifically, the invention has been described in some instances in the context of sugar mixtures resulting from hydrolysis of cellulose although similar mixtures produced by other methods are embodiments of the invention.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include", and "have" and their conjugates as used herein mean "including but not necessarily limited to".

EXAMPLES

Reference is now made to the following examples, which together with the above descriptions; illustrate the invention in a non limiting fashion.

Example 1

Chemical Analysis of Exemplary Compositions

Table 1 provides a summary of chemical analyses of six samples of sugar compositions according to exemplary embodiments of the invention. These compositions, when used in chemically catalyzed conversion processes can give results superior to those obtained in similar processes using previously available 42 DE sugar compositions.

TABLE 1 chemical analyses exemplary sugar compositions

| PARAMETER | SAMPLE | | | | | |
|---|---|---|---|---|---|---|
| | S2011080801 | S2011081001 | S2011081301 | S2011081601 | S11060601 | S11060602 |
| | | RESULT** | | | | |
| APPEARANCE | Clear colorless liquid*** | Clear colorless liquid | Colorless liquid | Clear colorless liquid*** | Colorless viscous liquid | Colorless viscous liquid |
| DS** | 76% | 78% | 77% | 80% | 69% | 73% |
| Monomeric sugars (total) | 94.3% | 94.1% | 93.5% | 93.6% | 89.7% | 87.3 |
| XYLOSE | 10.5% | 10.7% | 11.1% | 9.9% | 13.0% | 12.5% |
| ARABINOSE | 3.0% | 3.0% | 3.2% | 2.7% | 4.26% | 4.20% |
| MANNOSE | 25.4% | 26.1% | 25.3% | 25.0% | 26.4% | 25.8% |
| GLUCOSE | 50.5% | 49.6% | 49.2% | 50.9% | 38.2% | 37.3% |
| GALACTOSE | 4.7% | 4.7% | 4.8% | 4.5% | 7.80% | 7.54% |
| FRUCTOSE | Not detected | Not detected | Not detected | Not detected | Not detected | Not detected |
| GENTIOBIOSE | Not detected | Not detected | Not detected | Not detected | Not detected | Not detected |
| CELLOBIOSE | 0.6% | 0.4% | 0.4% | 0.3% | Not detected | Not detected |
| ISOMALTOSE | 0.2% | 0.2% | 0.3% | 0.3% | 0.26% | 0.09% |
| MALTOSE | Not detected | Not detected | Not detected | Not detected | Not detected | Not detected |
| TREHALOSE | 1.0% | 1.0% | 0.06% | 1.0% | 1.25% | 1.35% |
| dimeric sugars(other) | 3.9% | 4.9% | 4.9% | 4.9% | 5.08% | 5.40% |
| trimeric or longer sugars | Not detected | Not detected | Not detected | Not detected | Not detected | Not detected |
| FURFURAL DERIVATIVES | Not detected | Not detected | Not detected | Not detected | Not detected (<0.001%) | Not detected (<0.001%) |
| ACETIC ACID | Not detected | Not detected | Not detected | Not detected | 0.033% | 0.047% |
| ASH | 0.094% | 0.088% | 0.117% | 0.097% | | |

**All saccharides results refer to the dry solids (DS).
***At ambient temperature the product may appear as white opaque liquid, but becomes clearer upon warming.

Example 2

Chemical Analysis of Ash Fraction of Exemplary Compositions

Table 2 provides a summary of chemical analyses of the ash fraction from the first four samples presented in Table 1.

TABLE 2 chemical analyses of ash fraction of exemplary sugar compositions

| Ion | SAMPLE | | | |
|---|---|---|---|---|
| | S2011080801 | S2011081001 | S2011081301 | S2011081601 |
| | RESULT (PPM of total solids) | | | |
| Ca | <1 | <1 | <1 | <1 |
| Cu | <1 | <1 | <1 | <1 |
| Fe | <1 | <1 | <1 | <1 |
| K | 10 | 10 | 11 | 11 |
| Mg | <1 | <1 | <1 | <1 |
| Mn | <1 | <1 | <1 | <1 |
| Na | 42 | 38 | 34 | 43 |
| P | <1 | <1 | <1 | <1 |
| S | 7 | 6 | 7 | 7 |
| Si | 154 | 152 | 146 | 163 |

Results presented in Table 2 indicate that sulfur and phosphorus levels in the analyzed samples are exceptionally low.

These results suggest that the exemplary sugar compositions analyzed will exhibit a low tendency to foul and/or poison catalysts employed in the relevant conversion processes.

The invention claimed is:

1. A composition comprising:
  (a) at least one water-soluble monomeric cellulose sugar hydrolyzate;
  (b) at least one water-soluble monomeric hemicellulose sugar hydrolyzate;
  (c) at least one water-soluble dimeric or higher oligomeric hemicellulose sugar hydrolyzate; and
  (d) less than 2500 ppm in total by weight, relative to the total solids in the composition, of ash, wherein the ash comprises Ca, Cu, Fe, K, Mg, Mn, Na, P, S, and Si.

2. The composition of claim 1, further comprising:
  at least one water-soluble dimeric or higher oligomeric cellulose sugar hydrolyzate.

3. The composition of claim 2, wherein:
  the water-soluble dimeric or higher oligomeric cellulose sugar hydrolyzate is selected from one of cellobiose, isomaltose, trehalose, or a combination thereof.

4. The composition of claim 1, further comprising:
  glucose, mannose, galactose, fructose, or a combination thereof.

5. The composition of claim 1, wherein the water-soluble monomeric hydrolyzates are derived from a lignocellulose substrate.

6. The composition of claim 1, further comprising water.

7. The composition of claim 1, wherein the water-soluble monomeric hydrolyzates are present at a concentration of at least 360 g/L in an aqueous solution.

8. The composition of claim 1, wherein the water-soluble monomeric cellulose sugar hydrolyzate is glucose.

9. The composition of claim 1, further comprising less than 1000 ppm by weight, relative to the total solids in the composition, of ash.

10. The composition of claim 1, further comprising less than 1 ppm by weight, based on the total weight of the total solids in the composition, of calcium.

11. The composition of claim 1, further comprising less than 1 ppm by weight, based on the total weight of the total solids in the composition, of iron.

12. The composition of claim 1, further comprising less than 50 ppm by weight, based on the total weight of the total solids in the composition, of sulfur.

13. The composition of claim 1, wherein the weight ratio of the water-soluble monomeric hydrolyzates to the ash is greater than about 360:1.

14. A composition comprising:
  (a) at least one water-soluble monomeric cellulose sugar hydrolyzate;
  (b) at least one water-soluble monomeric hemicellulose sugar hydrolyzate;
  (c) at least one water-soluble dimeric or higher oligomeric hemicellulose sugar hydrolyzate; and
  (d) impurities, wherein the impurities comprise:
    less than 1 ppm by weight, based on the total weight of the total solids in the composition, of calcium;
    less than 1 ppm by weight, based on the total weight of the total solids in the composition, of iron;
    less than 51 ppm by weight, based on the total weight of the total solids in the composition, of sulfur; and
    less than 2500 ppm by weight, based on the total weight of the total solids in the composition, of ash.

15. The composition of claim 14, wherein the impurities comprise Ca, Cu, Fe, K, Mg, Mn, Na, P, S, and Si.

16. The composition of claim 14, further comprising:
  at least one water-soluble dimeric or higher oligomeric cellulose sugar hydrolyzate.

17. The composition of claim 16, wherein:
  the water-soluble dimeric or higher oligomeric cellulose sugar hydrolyzate is selected from one of cellobiose, isomaltose, trehalose, or a combination thereof.

18. The composition of claim 14, further comprising glucose, mannose, galactose, fructose, or a combination thereof.

19. The composition of claim 14, further comprising less than 1000 ppm by weight, relative to the total solids in the composition, of ash, wherein the ash comprises Ca, Cu, Fe, K, Mg, Mn, Na, P, S, and Si.

20. The composition of claim 1, comprising at least one dimeric hydrolyzate.

21. The composition of claim 1, wherein:
  the water-soluble monomeric hemicellulose sugar hydrolyzate is selected from one of xylose, arabinose, or a combination thereof; and
  the water-soluble dimeric or higher oligomeric hemicellulose sugar hydrolyzate is selected from one of a dimer or higher oligomer of xylose, arabinose, or a combination thereof.

22. The composition of claim 9, wherein:
  the water-soluble monomeric hemicellulose sugar hydrolyzate is selected from one of xylose, arabinose, or a combination thereof; and
  the water-soluble dimeric or higher oligomeric hemicellulose sugar hydrolyzate is selected from one of a dimer or higher oligomer of xylose, arabinose, or a combination thereof.

23. The composition of claim 10, wherein:
  the water-soluble monomeric hemicellulose sugar hydrolyzate is selected from one of xylose, arabinose, or a combination thereof; and the water-soluble dimeric or higher oligomeric hemicellulose sugar hydrolyzate is selected from one of a dimer or higher oligomer of xylose, arabinose, or a combination thereof.

24. The composition of claim 11, wherein:
the water-soluble monomeric hemicellulose sugar hydrolyzate is selected from one of xylose, arabinose, or a combination thereof; and
the water-soluble dimeric or higher oligomeric hemicellulose sugar hydrolyzate is selected from one of a dimer or higher oligomer of xylose, arabinose, or a combination thereof.

25. The composition of claim 12, wherein:
the water-soluble monomeric hemicellulose sugar hydrolyzate is selected from one of xylose, arabinose, or a combination thereof; and
the water-soluble dimeric or higher oligomeric hemicellulose sugar hydrolyzate is selected from one of a dimer or higher oligomer of xylose, arabinose, or a combination thereof.

26. A composition comprising:
at least one water-soluble monosaccharide cellulose sugar hydrolyzate;
at least one water-soluble monosaccharide hemicellulose sugar hydrolyzate;
at least one water-soluble disaccharide hemicellulose sugar hydrolyzate; and
less than 2500 ppm in total by weight, relative to the total solids in the composition, of ash, wherein the ash comprises Ca, Cu, Fe, K, Mg, Mn, Na, P, S, and Si.

27. A composition, comprising:
at least one water-soluble C6 monosaccharide hydrolyzate;
at least one water-soluble C5 monosaccharide hydrolyzate;
at least one water-soluble C5 oligosaccharide hydrolyzate having a degree of polymerization of about 2 to about 10; and
impurities; wherein said impurities comprise:
less than about 2500 ppm in total by weight of ash; wherein said ash comprises Ca, Cu, Fe, K, Mg, Mn, Na, P, S, and Si.

28. The composition of claim 27,
wherein said water-soluble C6 monosaccharide hydrolyzate is extracted from lignocellulosic biomass.

29. The composition of claim 27, further comprising: water.

30. The composition of claim 27,
wherein said water-soluble C6 monosaccharide hydrolyzate is present at a concentration of at least 360 g/L.

31. The composition of claim 27,
wherein said water-soluble C6 monosaccharide hydrolyzate is glucose, galactose, mannose, fructose, or a mixture thereof.

32. The composition of claim 27, further comprising:
less than about 1 ppm by weight of calcium.

33. The composition of claim 27, further comprising:
less than about 1 ppm by weight of iron.

34. The composition of claim 27, further comprising:
less than about 50 ppm by weight of sulfur.

35. The composition of claim 27,
wherein the weight ratio of said water-soluble C6 monosaccharide hydrolyzate to said elements is greater than about 360:1.

36. A composition, comprising:
at least one water-soluble C6 monosaccharide hydrolyzate;
at least one water-soluble C5 monosaccharide hydrolyzate;
at least one water-soluble C5 oligosaccharide hydrolyzate having a degree of polymerization of about 2 to about 10; and
impurities; wherein said impurities comprise:
less than 2500 ppm in total by weight of ash; and
less than about 1 ppm by weight of calcium.

37. A composition, comprising:
at least one water-soluble C6 monosaccharide hydrolyzate;
at least one water-soluble C5 monosaccharide hydrolyzate;
at least one water-soluble C5 oligosaccharide hydrolyzate having a degree of polymerization of about 2 to about 10; and
impurities; wherein said impurities comprise:
less than 2500 ppm in total by weight of ash; and
less than about 1 ppm by weight of iron.

38. The composition of claim 37, further comprising:
less than about 50 ppm by weight of sulfur.

39. A composition, comprising:
at least one water-soluble C6 monosaccharide hydrolyzate;
at least one water-soluble C5 monosaccharide hydrolyzate;
at least one water-soluble C5 oligosaccharide hydrolyzate having a degree of polymerization of about 2 to about 10; and
impurities; wherein said impurities comprise:
less than 2500 ppm in total by weight of ash; and
less than about 50 ppm by weight of sulfur.

* * * * *

UNITED STATES PATENT AND TRADEMARK OFFICE
CERTIFICATE OF CORRECTION

PATENT NO. : 9,976,194 B2
APPLICATION NO. : 14/730125
DATED : May 22, 2018
INVENTOR(S) : Aharon Eyal et al.

Page 1 of 1

It is certified that error appears in the above-identified patent and that said Letters Patent is hereby corrected as shown below:

In the Claims

Claim 14, Column 20, Line 26, delete "less than 51 ppm" and insert -- less than 50 ppm --.

Signed and Sealed this
Twenty-fifth Day of September, 2018

Andrei Iancu
*Director of the United States Patent and Trademark Office*